(12) United States Patent
Molt et al.

(10) Patent No.: US 8,258,297 B2
(45) Date of Patent: Sep. 4, 2012

(54) TRANSITION METAL COMPLEXES WITH BRIDGED CARBENE LIGANDS AND USE THEREOF IN OLEDS

(75) Inventors: Oliver Molt, Hirschberg (DE);
Christian Lennartz, Schifferstadt (DE);
Evelyn Fuchs, Mannheim (DE); Klaus Kahle, Ludwigshafen (DE); Nicolle Langer, Heppenheim (DE); Christian Schildknecht, Mannheim (DE); Jens Rudolph, Worms (DE); Gerhard Wagenblast, Wachenheim (DE); Soichi Watanabe, Mannheim (DE)

(73) Assignee: BASF SE, Ludwigshafen (DE)

( * ) Notice: Subject to any disclaimer, the term of this patent is extended or adjusted under 35 U.S.C. 154(b) by 293 days.

(21) Appl. No.: 12/738,104

(22) PCT Filed: Oct. 17, 2008

(86) PCT No.: PCT/EP2008/064064
§ 371 (c)(1),
(2), (4) Date: Apr. 15, 2010

(87) PCT Pub. No.: WO2009/050281
PCT Pub. Date: Apr. 23, 2009

(65) Prior Publication Data
US 2010/0264405 A1  Oct. 21, 2010

(30) Foreign Application Priority Data

Oct. 17, 2007  (EP) .................................. 07118675
Mar. 26, 2008  (EP) .................................. 08153303

(51) Int. Cl.
C07F 15/00 (2006.01)
H01L 51/50 (2006.01)

(52) U.S. Cl. ........................ 546/10; 313/504; 428/690

(58) Field of Classification Search .................... 546/10; 313/504; 428/690
See application file for complete search history.

(56) References Cited

U.S. PATENT DOCUMENTS

| 2006/0258043 A1 | 11/2006 | Bold et al. |
| 2008/0018221 A1 | 1/2008 | Egen et al. |
| 2009/0018330 A1 | 1/2009 | Molt et al. |
| 2009/0054657 A1 | 2/2009 | Molt et al. |
| 2010/0213834 A1 | 8/2010 | Molt et al. |

FOREIGN PATENT DOCUMENTS

| WO | 02 15645 | 2/2002 |
| WO | 2005 019373 | 3/2005 |
| WO | 2005 113704 | 12/2005 |
| WO | 2006 056418 | 6/2006 |
| WO | 2007 088093 | 8/2007 |
| WO | 2007 095118 | 8/2007 |
| WO | 2007 115981 | 10/2007 |
| WO | 2008 034758 | 3/2008 |
| WO | 2009 003898 | 1/2009 |
| WO | 2009 003919 | 1/2009 |

OTHER PUBLICATIONS

U.S. Appl. No. 12/667,765, filed Jan. 5, 2010, Langer, et al.

Primary Examiner — Charanjit Aulakh
(74) Attorney, Agent, or Firm — Oblon, Spivak, McClelland, Maier & Neustadt, L.L.P.

(57) ABSTRACT

Bridged cyclometalated carbene complexes, a process for preparing the bridged cyclometalated carbene complexes, the use of the bridged cyclometalated carbene complexes in organic light-emitting diodes, organic light-emitting diodes comprising at least one inventive bridged cyclometalated carbene complex, a light-emitting layer comprising at least one inventive bridged cyclometalated carbene complex, organic light-emitting diodes comprising at least one inventive light-emitting layer and devices which comprise at least one inventive organic light-emitting diode.

19 Claims, No Drawings

TRANSITION METAL COMPLEXES WITH BRIDGED CARBENE LIGANDS AND USE THEREOF IN OLEDS

The present invention relates to bridged cyclometalated carbene complexes, to a process for preparing the bridged cyclometalated carbene complexes, to the use of the bridged cyclometalated carbene complexes in organic light-emitting diodes, to organic light-emitting diodes comprising at least one inventive bridged cyclometalated carbene complex, to a light-emitting layer comprising at least one inventive bridged cyclometalated carbene complex, to organic light-emitting diodes comprising at least one inventive light-emitting layer and to devices which comprise at least one inventive organic light-emitting diode.

Organic light-emitting diodes (OLEDs) exploit the property of materials of emitting light when they are excited by electrical current. OLEDs are of interest especially as an alternative to cathode ray tubes and liquid-crystal displays for the production of flat visual display units. Owing to the very compact design and the intrinsically low power consumption, the devices comprising OLEDs are suitable especially for mobile applications, for example for uses in cellphones, laptops, etc.

The basic principles of the way in which OLEDs work and suitable assemblies (layers) of OLEDs are specified, for example, in WO 2005/113704 and the literature cited therein.

The prior art has already proposed numerous materials which emit light on excitation by electrical current.

WO 2005/019373 for the first time discloses the use of uncharged transition metal complexes which comprise at least one carbene ligand in OLEDs. According to WO 2005/019373, these transition metal complexes can be used in any layer of an OLED, the ligand structure or central metal being variable for adjustment to desired properties of the transition metal complexes. For example, the use of the transition metal complexes in a blocking layer for electrons, a blocking layer for excitons, a blocking layer for holes, or the light-emitting layer of the OLED is possible, preference being given to using the transition metal complexes as emitter molecules in OLEDs.

WO 2006/056418 discloses the use of uncharged transition metal-carbene complexes, wherein the carbene ligand used may be a bridged carbene ligand. Suitable bridged carbene ligands have the following general formula:

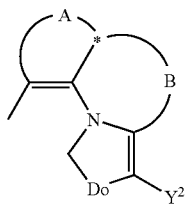

where the asterisk denotes the carbon atom or suitable heteroatom of the bridge A in the α position to the n-bonded vinylic carbon atom, and B denotes the bridge composed of an alkyl, alkenyl, alkynyl, aryl or heteroaryl radical ($Y^1$) and a chemical single bond, $C(Y^4)_2$, $C(O)$, O, S, $S(O)$, $SO_2$ or $NY^5$.

WO 2005/113704 relates to carbene-metal complexes for use in OLEDs. Among the numerous suitable carbene ligands mentioned, two bridged ligands are mentioned:

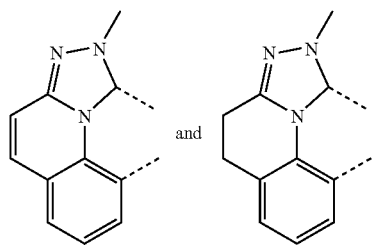

Application WO 2007/115981, which has an earlier priority date but had not been published at the priority date of the present application, discloses heteroleptic carbene complexes comprising both carbene ligands and heterocyclic non-carbene ligands. The carbene ligands may be bridged carbene ligands, and the bridged carbene ligands mentioned include those of the following formulae:

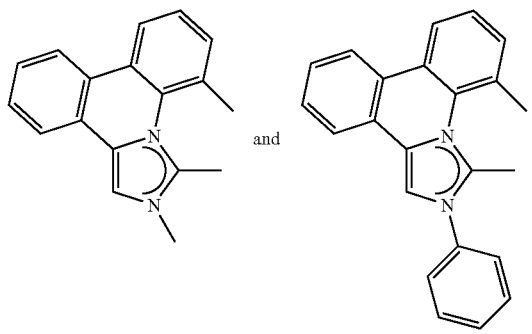

WO 2007/095118 relates to metal complexes of cyclometalated imidazo[1,2-f]phenanthridine and diimidazo[1,2-a:1',2'-c]quinazoline ligands, and also isoelectronic and benzo-fused analogs thereof. According to WO 2007/095118, blue-phosphorescing OLEDs with prolonged lifetime are to be provided.

Even though bridged carbene complexes which are suitable for use in OLEDs, especially as light-emitting substances, are already known, the provision of more stable and/or more efficient compounds which are usable industrially is desirable.

In the context of the present application, electroluminescence is understood to mean both electrofluorescence and electrophosphorescence.

It is therefore an object of the present application to provide bridged carbene complexes which are suitable for use in OLEDs. In particular, the provision of transition metal complexes which exhibit a property spectrum improved over known transition metal complexes, for example improved efficiencies and/or an improved lifetime/stability, is desirable.

This object is achieved by the provision of bridged cyclometalated carbene complexes of the general formula (I)

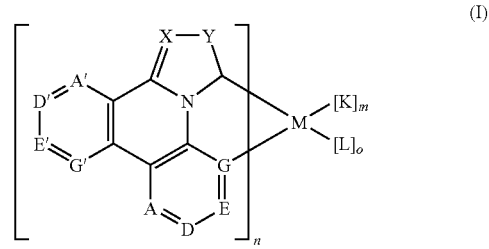

(I)

in which the symbols are each defined as follows:

M is a metal atom selected from the group consisting of metals of group IB, IIB, IIIB, IVB, VB, VIIB, VIIB, VIIIB, the lanthanides and IIIA of the Periodic Table of the Elements (CAS version) in any oxidation state possible for the appropriate metal atom; preferably Fe, Os, Co, Rh, Ir, Ni, Ru, Pd and Pt, Cu, Au, Ce, Tb, Eu, more preferably Os, Ru, Rh, Ir and Pt and most preferably Ir, Os and Pt;

K is an uncharged mono- or bidentate ligand;

L is a mono- or dianionic ligand, preferably a monoanionic ligand, which may be mono- or bidentate;

X is $CR^1$ or N, preferably N;

Y is $NR^2$ or $CR^2_2$;

A, D, G, E, A', D', G' and E'
are each independently CH, $CR^3$ or N;

$R^1$ is F, CN, $C_1$-$C_{20}$-alkoxy, $C_6$-$C_{30}$-aryloxy, $C_1$-$C_{20}$-alkylthio, $C_6$-$C_{30}$-arylthio, substituted or unsubstituted $C_6$-$C_{30}$-aryl or substituted or unsubstituted heteroaryl having from 5 to 30 ring atoms;

$R^2$, $R^3$
are each independently substituted or unsubstituted $C_1$-$C_{20}$-alkyl, substituted or unsubstituted $C_5$-$C_{20}$-cycloalkyl, substituted or unsubstituted $C_5$-$C_{20}$-cycloalkenyl, substituted or unsubstituted heterocycloalkyl having from 5 to 30 ring atoms, substituted or unsubstituted heterocycloalkenyl having from 5 to 30 ring atoms, substituted or unsubstituted $C_2$-$C_{20}$-alkenyl, substituted or unsubstituted $C_2$-$C_{20}$-alkynyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals, carbonyl (—CO($R^4$)), carbonylthio (—C=O($SR^4$)), carbonyloxy (—C=O($OR^4$)), oxycarbonyl (—OC=O($R^4$)), thiocarbonyl (—SC=O($R^4$)), amino (—$NR^4R^5$), OH, pseudohalogen radicals, amido (—CO=O($NR^4R^5$)), —$NR^4$C=O($R^5$), phosphonate (—P(O)($OR^4$)$_2$), phosphate (—OP(O)($OR^4$)$_2$), phosphine (—$PR^4R^5$), phosphine oxide (—P(O)$R^4_2$), sulfate (—OS(O)$_2$$OR^4$), sulfoxide (—S(O)$R^4$), sulfonate (—S(O)$_2$$OR^4$), sulfonyl (—S(O)$_2$$R^4$), sulfonamide (—S(O)$_2$$NR^4R^5$), $NO_2$, boronic esters (—B($OR^4$)$_2$), imino (—C=$NR^4R^5$), borane radicals, stannate radicals, hydrazine radicals, hydrazone radicals, oxime radicals, nitroso groups, diazo groups, vinyl groups, sulfoximines, alanes, germanes, boroxines and borazines;

or two adjacent $R^3$ radicals together form a saturated or unsaturated, substituted or unsubstituted bridge composed of from 3 to 6 atoms, such that the $R^3$ radicals together with one of the elements A=D, D-E, A'=D', D'-E', E'=G' form a 5- to 8-membered ring;

or the $R^3$ radicals at the G' and A positions together form a saturated or unsaturated, substituted or unsubstituted bridge composed of from 1 to 4 atoms, such that the $R^3$ radicals together with the element -G'-C=C-A- form a 5- to 8-membered ring;

$R^4$, $R^5$, $R^6$
are each independently H, substituted or unsubstituted $C_1$-$C_{20}$-alkyl or substituted or unsubstituted $C_6$-$C_{30}$-aryl or substituted or unsubstituted heteroaryl having from 5 to 30 ring atoms;

n is the number of carbene ligands, where n is at least 1 and the carbene ligands in the complex of the formula I, when n>1, may be the same or different;

m is the number of ligands K, where m may be 0 or $\geq$1, and the ligands K, when m>1, may be the same or different;

o is the number of ligands L, where o may be 0 or 1, and the ligands L, when o>1, may be the same or different;

where the sum of n+m+o depends on the oxidation state and coordination number of the metal atom used and on the denticity of the ligands L and K, and also on the charge of the ligands L, with the condition that n is at least 1.

The inventive bridged cyclometalated carbene complexes of the formula I are notable in that they have a bridge of the carbene ligand(s) and, especially in the X position, a nitrogen atom or a —C—F, —C—CN, —C—$C_1$-$C_{20}$-alkoxy, —C—$C_6$-$C_{30}$-aryloxy, —C—$C_1$-$C_{20}$-alkylthio, —C—$C_6$-$C_{30}$-arylthio, substituted or unsubstituted —C—$C_6$-$C_{30}$-aryl or substituted or unsubstituted —C-heteroaryl radical having from 5 to 30 ring atoms. It has been found that the inventive carbene complexes are notable for good stability and, with the aid of the inventive carbene complexes of the formula I, OLEDs are obtainable with an improved property spectrum, for example improved efficiencies and/or an improved lifetime.

Substituted or unsubstituted $C_1$-$C_{20}$-alkyl is understood to mean alkyl radicals having from 1 to 20 carbon atoms. Preference is given to $C_1$- to $C_{10}$-alkyl radicals, particular preference to $C_1$- to $C_6$-alkyl radicals. The alkyl radicals may be either straight-chain or branched. In addition, the alkyl radicals may be substituted by one or more substituents selected from the group consisting of $C_1$-$C_{20}$-alkyl, $C_1$-$C_{20}$-alkoxy, halogen, preferably F, $C_1$-$C_{20}$-haloalkyl, e.g. $CF_3$, and $C_6$-$C_{30}$-aryl, which may in turn be substituted or unsubstituted. Suitable aryl substituents and suitable alkoxy and halogen substituents are specified below. Examples of suitable alkyl groups are methyl, ethyl, propyl, butyl, pentyl, hexyl, heptyl and octyl, and also derivatives of the alkyl groups mentioned substituted by $C_1$-$C_{20}$-alkyl, $C_6$-$C_{30}$-aryl, $C_1$-$C_{20}$-alkoxy and/or halogen, especially F, for example $CF_3$. This also comprises both the n-isomers of the radicals mentioned and branched isomers such as isopropyl, isobutyl, isopentyl, sec-butyl, tert-butyl, neopentyl, 3,3-dimethylbutyl, 3-ethylhexyl, etc. Preferred alkyl groups are methyl, ethyl, isopropyl, tert-butyl and $CF_3$.

Substituted or unsubstituted $C_5$-$C_{20}$-cycloalkyl is understood to mean cycloalkyl groups having from 5 to 20, preferably from 5 to 10, more preferably from 5 to 8 carbon atoms in the base skeleton (ring). Suitable substituents are the substituents mentioned for the alkyl groups. Examples of suitable cycloalkyl groups, which may be unsubstituted or substituted by the radicals specified above for the alkyl groups, are cyclopentyl, cyclohexyl, cycloheptyl, cyclooctyl, cyclononyl and cyclodecyl. If appropriate, they may also be polycyclic ring systems such as decalinyl, norbornyl, bornanyl or adamantyl.

Substituted or unsubstituted $C_5$-$C_{20}$-cycloalkenyl is understood to mean cycloalkenyl groups having from 5 to 20, preferably from 5 to 10, more preferably from 5 to 8 carbon atoms in the base skeleton (ring). Suitable substituents are the substituents mentioned for the alkyl groups. The cycloalkenyl groups may have one double bond or—depending on the ring size—more than one double bond within the cycloalkenyl ring. The double bonds may be conjugated or nonconjugated. The cycloalkenyl groups preferably have one double bond within the cycloalkenyl ring. Examples of suitable cycloalkenyl groups, which may be unsubstituted or substituted by the radicals specified above for the alkyl groups, are cyclopentenyl, cyclohexenyl, cycloheptenyl, cyclooctenyl, cyclononenyl and cyclodecenyl. If appropriate, they may also be polycyclic ring systems, in which case at least one of the rings is a cycloalkenyl ring.

Substituted or unsubstituted heterocycloalkyl having from 5 to 30 ring atoms is understood to mean heterocycloalkyl groups having from 5 to 30, preferably from 5 to 10, more preferably from 5 to 8 ring atoms, at least one carbon atom in the heterocycloalkyl base skeleton being replaced by a heteroatom. Preferred heteroatoms are N, O and S. Suitable substituents are the substituents mentioned for the alkyl groups. Examples of suitable heterocycloalkyl groups, which may be unsubstituted or substituted by the radicals specified above for the alkyl groups, are radicals derived from the following heterocycles: pyrrolidine, thiolane, tetrahydrofuran, 1,2-oxathiolane, oxazolidine, piperidine, thiane, oxane, dioxane, 1,3-dithiane, morpholine, piperazine. If appropriate, they may also be polycyclic ring systems.

Substituted or unsubstituted heterocycloalkenyl having from 5 to 30 ring atoms is understood to mean heterocycloalkenyl groups having from 5 to 30, preferably from 5 to 10, more preferably from 5 to 8 ring atoms, at least one carbon atom in the heterocycloalkenyl base skeleton being replaced by a heteroatom and at least one double bond being present in the heterocycloalkenyl base skeleton. The heterocycloalkenyl groups may have one double bond or—depending on the ring size—more than one double bond within the heterocycloalkenyl ring. The double bonds may be conjugated or nonconjugated. The heterocycloalkenyl groups preferably have one double bond within the heterocycloalkenyl ring. Preferred heteroatoms are N, O and S. Suitable substituents are the substituents mentioned for the alkyl groups.

Substituted or unsubstituted $C_2$-$C_{20}$-alkenyl is understood to mean alkenyl radicals having from 2 to 20 carbon atoms. Preference is given to $C_2$- to $C_{10}$-alkenyl radicals, particular preference to $C_2$- to $C_6$-alkenyl radicals. The alkenyl radicals may be either straight-chain or branched. In addition, the alkenyl radicals may be substituted by one or more of the substituents mentioned for the alkyl radicals. The alkenyl radicals may—depending on the chain length—have one or more double bonds, in which case the double bonds may be conjugated to one another or be isolated from one another. Examples of suitable alkenyl groups are ethenyl, propenyl, butenyl, pentenyl, hexenyl, heptenyl and octenyl, where the double bond may be present at any position in the aforementioned radicals, and also derivatives of the alkenyl groups mentioned substituted by $C_1$-$C_{20}$-alkyl, $C_1$-$C_{20}$-haloalkyl, $C_6$-$C_{30}$-aryl, $C_1$-$C_{20}$-alkoxy and/or halogen, especially F.

Substituted or unsubstituted $C_2$-$C_{20}$-alkynyl is understood to mean alkynyl radicals having from 2 to 20 carbon atoms. Preference is given to $C_2$- to $C_{1-10}$-alkynyl radicals, particular preference to $C_2$- to $C_6$-alkynyl radicals. The alkynyl radicals may be either straight-chain or branched. In addition, the alkynyl radicals may be substituted by one or more of the substituents mentioned for the alkyl radicals. The alkynyl radicals may—depending on the chain length—have one or more triple bonds, in which case the triple bonds may be conjugated to one another or be isolated from one another. Examples of suitable alkynyl groups are ethynyl, propynyl, butynyl, pentynyl, hexynyl, heptynyl and octyntyl, where the triple bond may be present at any position in the aforementioned radicals, and also derivatives of the alkynyl groups mentioned substituted by $C_1$-$C_{20}$-alkyl, $C_1$-$C_{29}$-haloalkyl, $C_6$-$C_{30}$-aryl, $C_1$-$C_{20}$-alkoxy and/or halogen, especially F.

Suitable $C_1$-$C_{20}$-alkoxy and $C_1$-$C_{20}$-alkylthio groups derive correspondingly from the aforementioned $C_1$-$C_{20}$-alkyl radicals. Examples here include $OCH_3$, $OC_2H_6$, $OC_3H_7$, $OC_4H_9$ and $OC_8H_{17}$, and $SCH_3$, $SC_2H_5$, $SC_3H_7$, $SC_4H_9$ and $SC_8H_{17}$. $C_3H_7$, $C_4H_9$ and $C_8H_{17}$ comprise both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

Suitable pseudohalogen radicals in the context of the present application are CN, SCN, OCN, $N_3$ and SeCN, preference being given to CN and SCN. Very particular preference is given to CN.

$C_6$-$C_{30}$-Aryl refers in the present invention to radicals which are derived from monocyclic, bicyclic or tricyclic aromatics and do not comprise any ring heteroatoms. When the systems are not monocyclic systems, the saturated form (perhydro form) or the partly unsaturated form (for example the dihydro form or tetrahydro form), where the particular forms are known and stable, is also possible for the second ring in the term "aryl". This means that the term "aryl" in the present invention also comprises, for example, bicyclic or tricyclic radicals in which either both or all three radicals are aromatic, and also bicyclic or tricyclic radicals in which only one ring is aromatic, and tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl.

The $C_6$-$C_{30}$-aryl radicals may be unsubstituted or substituted by one or more further radicals. Suitable further radicals are selected from the group consisting of $C_1$-$C_{20}$-alkyl, $C_6$-$C_{30}$-aryl or substituents with donor or acceptor action, suitable substituents with donor or acceptor action being specified below. The $C_6$-$C_{30}$-aryl radicals are preferably unsubstituted or substituted by one or more $C_1$-$C_{20}$-alkyl groups, $C_1$-$C_{20}$-alkoxy groups, CN, $CF_3$, F or amino groups ($NR^4R^5$ where suitable $R^4$ and $R^5$ radicals have been specified above). Further preferred substitutions of the $C_6$-$C_{30}$-aryl radicals depend on the end use of the compounds of the general formula (I) and are specified below.

Suitable $C_6$-$C_{30}$-aryloxy, $C_6$-$C_{30}$-arylthio radicals derive correspondingly from the aforementioned $C_6$-$C_{30}$-aryl radicals. Particular preference is given to phenoxy and phenylthio.

Unsubstituted or substituted heteroaryl having from 5 to 30 ring atoms is understood to mean monocyclic, bicyclic or tricyclic heteroaromatics which can be derived partly from the aforementioned aryl, in which at least one carbon atom in the aryl base skeleton has been replaced by a heteroatom. Preferred heteroatoms are N, O and S. More preferably, the heteroaryl radicals have 5 to 13 ring atoms. Especially preferably, the base skeleton of the heteroaryl radicals is selected from systems such as pyridine and five-membered heteroaromatics such as thiophene, pyrrole, imidazole, thiazole, oxazole or furan. These base skeletons may optionally be fused to one or two six-membered aromatic radicals. Suitable fused heteroaromatics are carbazolyl, benzimidazolyl, benzofuryl, benzothiazole, benzoxazole, dibenzofuryl or dibenzothiophenyl.

The base skeleton may be substituted at one, more than one or all substitutable positions, suitable substituents being the same as have already been mentioned under the definition of $C_6$-$C_{30}$-aryl. However, the heteroaryl radicals are preferably unsubstituted. Suitable heteroaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl, thiazol-2-yl, oxazol-2-yl and imidazol-2-yl, and the corresponding benzofused radicals, especially carbazolyl, benzimidazolyl, benzofuryl, benzothiazole, benzoxazole, dibenzofuryl or dibenzothiophenyl.

In the context of the present application, groups with donor or acceptor action are understood to mean the following groups:

$C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals, carbonyl (—CO($R^4$)), carbonylthio (—C=O ($SR^4$)), carbonyloxy (—C=O($OR^4$)), oxycarbonyl (—OC=O($R^4$)), thiocarbonyl (—SC=O($R^4$)), amino (—$NR^4R^5$), OH, pseudohalogen radicals, amido (—C=O ($NR^4R^5$)), —$NR^4$C=O($R^5$), phosphonate (—P(O)($OR^4$)$_2$), phosphate (—OP(O)($OR^4$)$_2$), phosphine (—$PR^4R^5$), phosphine oxide (—P(O)$R^4{}_2$), sulfate (—OS(O)$_2OR^4$), sulfoxide (—S(O)$R^4$), sulfonate (—S(O)$_2OR^4$), sulfonyl (—S(O)$_2R^4$), sulfonamide (—S(O)$_2NR^4R^5$), NO$_2$, boronic esters (—OB ($OR^4$)$_2$), imino (—C=$NR^4R^5$), borane radicals, stannate radicals, hydrazine radicals, hydrazone radicals, oxime radicals, nitroso groups, diazo groups, vinyl groups, sulfoximines, alanes, germanes, boroxines and borazines.

Preferred substituents with donor or acceptor action are selected from the group consisting of:

$C_1$-$C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^4R^5R^6$ where $R^4$, $R^5$ and $R^6$ are preferably each independently substituted or unsubstituted alkyl or substituted or unsubstituted phenyl, suitable substituents having been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —C(O)O$C_1$-$C_4$-alkyl, preferably —C(O) OMe, P(O)R$_2$, preferably P(O)Ph$_2$ and SO$_2$R$_2$, preferably SO$_2$Ph.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^4R^5R^6$ where suitable $R^4$, $R^5$ and $R^6$ radicals have already been specified, diphenylamino, —C(O)O$C_1$-$C_4$-alkyl, preferably —C(O)OMe, P(O)Ph$_2$ and SO$_2$Ph.

The aforementioned groups with donor or acceptor action are not intended to rule out the possibility that further radicals and groups among those specified above may also have donor or acceptor action. For example, the aforementioned heteroaryl radicals are likewise groups with donor or acceptor action, and the $C_1$-$C_{20}$-alkyl radicals are groups with donor action.

The $R^4$, $R^5$ and $R^6$ radicals mentioned in the aforementioned groups with donor or acceptor action are each as already defined above, i.e. $R^4$, $R^5$ and $R^6$ are each independently:

Hydrogen, substituted or unsubstituted $C_1$-$C_{20}$-alkyl or substituted or unsubstituted $C_6$-$C_{30}$-aryl or substituted or unsubstituted heteroaryl having from 5 to 30 ring atoms, suitable and preferred alkyl and aryl radicals having been specified above. More preferably, the $R^4$, $R^5$ and $R^6$ radicals are each $C_1$-$C_6$-alkyl, e.g. methyl, ethyl, i-propyl, tert-butyl, or phenyl or pyridyl.

The metal atom M in the inventive bridged cyclometalated carbene complexes of the general formula I is selected from the group consisting of metals of group IB, IIB, IIIB, IVB, VB, VIIB, VIIB, VIIIB, the lanthanides and IIIA of the Periodic Table of the Elements (CAS version) in any oxidation state possible for the appropriate metal atom; preferably Fe, Os, Co, Rh, Ir, Ni, Ru, Pd and Pt, Cu, Au, Ce, Tb, Eu, more preferably Os, Ru, Rh, Ir and Pt and most preferably Ir, Os and Pt, in any oxidation state possible for the appropriate metal atom.

More preferably, the metal M is selected from the group consisting of Ir, Os and Pt, preference being given to Os(II), Ir(III) and Pt(II). Particular preference is given to Ir(II).

The number of carbene ligands n and the numbers m and o of any ligands K and L present depend on the oxidation state and the coordination number of the metal M, and on the denticity and the charge of the ligands L, where at least one carbene ligand is present in the inventive carbene complexes of the formula I, i.e. n is at least 1.

Preferred embodiments of inventive carbene complexes of the formula I depending on the charge and coordination number of the metal M used are described hereinafter:

In the case that M is a metal with a coordination number of 4 (e.g. Pt(II) or Pd(II), Rh(I)), the inventive carbene complexes of the formula I have one or two carbene ligands, i.e. n is 1 or 2, where, in the case that n is 1 and M is a metal with a coordination number of 4, one monoanionic bidentate ligand L is present as well as the carbene ligand in the inventive carbene complexes, i.e. o is 1. In the case that M is a metal with a coordination number of 6 (e.g. Ir(III), Co(II), Co(III), Rh(III), Os(II), Pt(IV)), the inventive carbene complexes of the formula I, depending on their charge, preferably have one, two or three, preferably two or three, carbene ligands of the general formula I which may be the same or different, i.e. n is 1, 2 or 3, preferably 2 or 3. For example, n in the case of Ir(III), Co(III) or Rh(III) is generally 1, 2 or 3, where, in the case that n=1, two additional monoanionic bidentate ligands L are present, i.e. o is 2. In the case that n=2, the aforementioned carbene complexes have one additional monoanionic bidentate ligand L, i.e. o is 1. In the case that n=3, which is particularly preferred, the aforementioned carbene complexes do not have any further ligands K and L, i.e. m and o are each 0. In the case of Os(II), n is generally 1 or 2, where, in the case that n=1, one additional monoanionic bidentate ligand L and one additional uncharged bidentate ligand K are present, i.e. o is 1 and m is 1. In the case that n=2, which is particularly preferred, the aforementioned carbene complexes have one additional uncharged bidentate ligand K, i.e. m is 1. When the metal atom M has a coordination number of 8 or more, the inventive carbene complexes of the general formula I, as well as one, two or three carbene ligands, may have either one or more further carbene ligands and/or one or more additional ligands K and/or L. In a preferred embodiment, the present invention relates to bridged cyclometalated carbene complexes of the general formula I which have a metal M with a coordination number of 6, preferably Ir(III), where n=3 and m and o are each 0.

Depending on the coordination number of the metal M used and the number n of carbene ligands used and the numbers m and o of the additional ligands K and L which may be used, different isomers of the corresponding metal complexes with the same metal M and the same nature of the carbene ligands used and additional may be present. For example, in the case of complexes with a metal M with coordination number 6 (i.e. octahedral complexes), for example Ir(III) complexes, "fac-mer isomers" (facial/meridional isomers) are possible when the complexes are those of the general composition M(AB)₃ where AB are bidentate ligands. In the context of the present application, "fac-mer isomers" are understood to mean the isomers shown below:

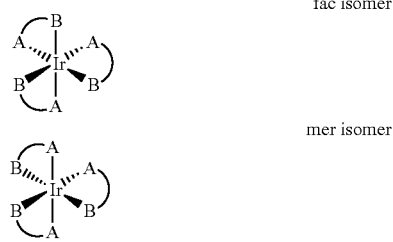

fac isomer mer isomer

In the case of square-planar complexes with a metal M with the coordination number of 4, for example Pt(II) complexes, "cis/trans isomers" are possible when the complexes are those of the general composition M(AB)₂, where AB are bidentate ligands. In the context of the present application "isomers" are understood to mean the isomers shown below:

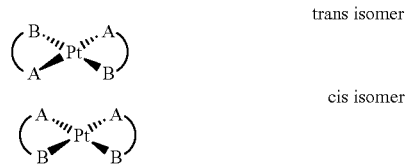

trans isomer cis isomer

The symbols A and B are each one binding site of a ligand, only bidentate ligands being present. According to the aforementioned general composition, a bidentate ligand has two A groups and two B groups.

It is known in principle to those skilled in the art what is meant by cis/trans and fac-mer isomers. In complexes of the composition MA₃B₃, three groups of the same type may either occupy the corners of one octahedral face (facial isomer) or a meridian, i.e. two of the three ligand binding sites are trans to one another (meridional isomer). With regard to the definition of cis/trans isomers and fac-mer isomers in octahedral metal complexes, see, for example, J. Huheey, E. Keiter, R. Keiter, Anorganische Chemie: Prinzipien von Struktur und Reaktivitat [Inorganic Chemistry: Principles of Structure and Reactivity], 2nd, newly revised edition, translated into German and extended by Ralf Steudel, Berlin; New York: de Gruyter, 1995, pages 575, 576.

In the case of square-planar complexes, cis-isomerism means that, in complexes of the composition MA₂B₂, both the two A groups and the two B groups occupy adjacent corners of a square, while both the two A groups and the two B groups in the case of trans isomerism each occupy the two mutually diagonally opposite corners of a square. With regard to the definition of cis/trans isomers in square-planar metal complexes, see, for example, J. Huheey, E. Keiter, R. Keiter, Anorganische Chemie: Prinzipien von Struktur und Reaktivität, 2nd, newly revised edition, translated into German and expanded by Ralf Steudel, Berlin; New York: de Gruyter, 1995, pages 557 to 559.

In general, the different isomers of the inventive carbene complexes of the formula I can be separated by processes known to those skilled in the art, for example by chromatography, sublimation or crystallization.

The present invention thus relates both to the individual isomers of the carbene complexes of the formula I in each case and to mixtures of different isomers in any mixing ratio.

The number n of carbene ligands in the inventive bridged cyclometalated carbene complexes of the formula I in which the transition metal atom M has a coordination number of 6 and the oxidation state of III, particular preference being given to Ir(III), is preferably 3, and the numbers m and o of the additional ligands K and L in these complexes are preferably each 0.

The number n of carbene ligands in the inventive bridged cyclometalated carbene complexes of the formula I in which the transition metal atom M has a coordination number of 6 and the oxidation state of II, particular preference being given to Os(II), is preferably 2, in which case one additional uncharged bidentate ligand K is present, i.e. m is preferably 1. o in these complexes is preferably 0.

The number n of carbene ligands in the inventive bridged cyclometalated carbene complexes of the formula I in which the transition metal atom M has a coordination number of 4, particular preference being given to Pt(II), is preferably 1 or 2, where, in the case that n=1, preferably one additional monoanionic bidentate ligand L is present, i.e. o is likewise preferably 1 and m is preferably O. In the case that n=2, m and o are preferably each 0.

In a very particularly preferred embodiment, M in the carbene complexes of the formula I is Ir(III), n is 3 and m and o are each 0.

The n carbene ligands in the carbene complex when n>1 may be the same or different. They are preferably the same, i.e., in the case that M=Ir(III) and n=3, the three carbene ligands are preferably the same.

Suitable mono- or dianionic ligands L, preferably monoanionic ligands L, which may be mono- or bidentate, are the ligands typically used as mono- or bidentate, mono- or dianionic ligands.

Suitable monoanionic monodentate ligands are, for example, halides, especially Cl⁻ and Br⁻, pseudohalides, especially CN⁻, cyclopentadienyl (Cp⁻), hydride, alkoxy, aryloxy, alkyl radicals which are bonded to the transition metal M via a sigma bond, for example CH₃, alkylaryl radicals which are bonded to the transition metal M¹ via a sigma bond, for example benzyl.

Suitable monoanionic bidentate ligands are, for example, acetylacetonate and derivatives thereof, picolinate, Schiff bases, amino acids, arylazoles, e.g. phenylpyridine, and the further bidentate monoanionic ligands specified in WO 02/15645, preference being given to acetylacetonate and picolinate.

Suitable dianionic bidentate ligands are, for example, dialkoxides, dicarbonates, dicarboxylates, diamides, diimides, dithiolates, biscyclopentadienyls, bisphosphonates, bissulfonates and 3-phenylpyrazole.

Suitable uncharged mono- or bidentate ligands K are preferably selected from the group consisting of phosphines, both mono- and bisphosphines; phosphonates, both mono- and bisphosphonates, and derivatives thereof, arsenates, both mono- and bisarsenates, and derivatives thereof; phosphites, both mono- and bisphosphites; CO; pyridines, both mono- and bispyridines; nitriles, dinitriles, allyl, diimines, unconjugated dienes and conjugated dienes which form a π-complex with M¹. Particularly preferred uncharged mono- or bidentate ligands K are selected from the group consisting of phosphines, both mono- and bisphosphines, preferably trialkyl-, triaryl- or alkylarylphosphines, more preferably PAr₃, where Ar is a substituted or unsubstituted aryl radical and the three aryl radicals in PAr₃ may be the same or different, more preferably PPh₃, PEt₃, PnBu₃, PEt₂Ph, PMe₂Ph, PnBu₂Ph; phosphonates and derivatives thereof, arsenates and derivatives thereof, phosphites, CO; pyridines, both mono- and bispyridines, where the pyridines may be substituted by alkyl or aryl groups; nitriles and dienes which form a π-complex with $M^1$, preferably $\eta^4$-diphenyl-1,3-butadiene, $\eta^4$-1,3-pentadiene, $\eta^4$-1-phenyl-1,3-pentadiene, $\eta^4$-1,4-dibenzyl-1,3-butadiene, $\eta^4$-2,4-hexadiene, $\eta^4$-3-methyl-1,3-pentadiene, $\eta^4$-1,4-ditolyl-1,3-butadiene, $\eta^4$-1,4-bis(trimethylsilyl)-1,3-butadiene and $\eta^2$- or $\eta^4$-cyclooctadiene (in each case 1,3 and in each case 1,5), more preferably 1,4-diphenyl-1,3-butadiene, 1-phenyl-1,3-pentadiene, 2,4-hexadiene, butadiene, $\eta^2$-cyclooctene, $\eta^4$-1,3-cyclooctadiene and $\eta^4$-1,5-cyclooctadiene. Very particularly preferred uncharged monodentate ligands are selected from the group consisting of $PPh_3$, $P(OPh)_3$, $AsPh_3$, CO, pyridine, nitriles and derivatives thereof. Suitable uncharged mono- or bidentate ligands are preferably 1,4-diphenyl-1,3-butadiene, 1-phenyl-1,3-pentadiene, 2,4-hexadiene, $\eta^4$-cyclooctadiene and $\eta^2$-cyclooctadiene (in each case 1,3 and in each case 1,5).

The $R^1$ radical of the X group in the cyclometalated carbene complexes of the formula I is F, CN, $C_1$-$C_{20}$-alkoxy, $C_6$-$C_{30}$-aryloxy, $C_1$-$C_{20}$-alkylthio, $C_6$-$C_{30}$-arylthio, substituted or unsubstituted $C_6$-$C_{30}$-aryl or substituted or unsubstituted heteroaryl having from 5 to 30 ring atoms. The $R^1$ radical of the X group is preferably F, CN, $C_1$- to $C_4$-alkoxy, more preferably methoxy, $C_6$- to $C_{10}$-aryloxy, more preferably phenoxy, $C_1$- to $C_4$-alkylthio, more preferably $SCH_3$, $C_6$- to $C_{1-10}$-arylthio, substituted or unsubstituted phenyl, more preferably unsubstituted phenyl, tolyl, dimethylphenyl, trimethylphenyl, F-, CN-, methoxy- and/or $CF_3$-substituted phenyl, or substituted or unsubstituted heteroaryl having from 5 to 13 ring atoms, more preferably pyridyl, thienyl, pyrrolyl, furyl, thiazolyl, oxazolyl, pyrazolyl or imidazolyl. Most preferably, the $R^1$ radical is F, CN or methoxy, phenyl, pyridyl.

The X group in the cyclometalated carbene complexes of the formula I is preferably N, i.e. the $R^1$ radical is absent.

The $R^2$ and $R^3$ radicals in the bridged cyclometalated carbene complexes of the formula I are each independently substituted or unsubstituted $C_1$-$C_{20}$-alkyl, substituted or unsubstituted $C_5$-$C_{20}$-cycloalkyl, substituted or unsubstituted $C_5$-$C_{20}$-cycloalkenyl, substituted or unsubstituted heterocycloalkyl having from 5 to 30 ring atoms or substituted or unsubstituted heterocycloalkenyl having from 5 to 30 ring atoms, substituted or unsubstituted $C_2$-$C_{20}$-alkenyl, substituted or unsubstituted $C_2$-$C_{20}$-alkynyl, substituted or unsubstituted $C_5$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_5$-$C_{30}$-arylthio, $SiR^4R^5R^6$, halogen radicals, halogenated $C_1$-$C_{20}$-alkyl radicals, carbonyl (—CO($R^4$)), carbonylthio (—C=O(S$R^4$)), carbonyloxy (—C=O(O$R^4$)), oxycarbonyl (—OC=O($R^4$)), thiocarbonyl (—SC=O($R^4$)), amino (—N$R^4R^5$), OH, pseudohalogen radicals, amido (—C=O(N$R^4R^5$)), —N$R^4$C=O($R^5$), phosphonate (—P(O)(O$R^4$)$_2$, phosphate (—OP(O)(O$R^4$)$_2$), phosphine (—P$R^4R^5$), phosphine oxide (—P(O)$R^4_2$), sulfate (—OS(O)$_2$O$R^4$), sulfoxide (—S(O)$R^4$), sulfonate (—S(O)$_2$O$R^4$), sulfonyl (—S(O)$_2R^4$), sulfonamide (—S(O)$_2$N$R^4R^5$), NO$_2$, boronic esters (—B(O$R^4$)$_2$), imino (—C=N$R^4R^5$), borane radicals, stannate radicals, hydrazine radicals, hydrazone radicals, oxime radicals, nitroso groups, diazo groups, vinyl groups, sulfoximines, alanes, germanes, boroxines and borazines;

or two adjacent $R^3$ radicals together form a saturated or unsaturated, substituted or unsubstituted bridge composed of from 3 to 6 atoms, such that the $R^3$ radicals together with one of the elements A=D, D-E, A'=D', D'-E', E'=G' form a 5- to 8-membered ring;

or the $R^3$ radicals at the G' and A positions together form a saturated or unsaturated, substituted or unsubstituted bridge composed of from 1 to 4 atoms, such that the $R^3$ radicals together with the element -G'-C—C-A- form a 5- to 8-membered ring;

the bridges are preferably unsubstituted (i.e. all substitutable positions are substituted by hydrogen) or substituted by one or more radicals selected from the group consisting of $C_1$-$C_4$-alkyl, more preferably methyl, ethyl, n-propyl, isopropyl, n-butyl, isobutyl, sec-butyl or tert-butyl, substituted or unsubstituted phenyl, preferably unsubstituted phenyl, tolyl, dimethylphenyl, trimethylphenyl, F-, CN-, methoxy- and/or $CF_3$-substituted phenyl, substituted or unsubstituted heteroaryl having from 5 to 13 ring atoms, preferably pyridyl, thienyl, pyrrolyl, furyl or imidazolyl, $C_1$-$C_4$-alkoxy, more preferably methoxy, $C_6$-$C_{10}$-aryloxy, particularly phenoxy, $C_1$-$C_4$-alkylthio, preferably $SCH_3$, $C_6$-$C_{10}$-arylthio, preferably SPh, $SiR^4R^5R^6$, preferably $SiMe_3$ or $SiPh_3$, F, Cl, Br, preferably F, halogenated $C_1$-$C_{10}$-alkyl radicals, preferably $CF_3$, and pseudohalogen radicals, preferably CN; where the bridges are preferably formed from carbon atoms and optionally have 1 or 2 heteroatoms, preferably 1 or 2 nitrogen atoms.

In a preferred embodiment, $R^2$ and $R^3$ are each independently selected from the group consisting of substituted or unsubstituted $C_1$-$C_{20}$-alkyl, substituted or unsubstituted $C_2$-$C_{20}$-alkenyl, substituted or unsubstituted $C_2$-$C_{20}$-alkynyl, substituted or unsubstituted $C_5$-$C_{30}$-aryl, substituted or unsubstituted heteroaryl having from 5 to 30 ring atoms, $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals and pseudohalogen radicals. More preferably, $R^2$ and $R^3$ are each independently selected from the group consisting of substituted or unsubstituted $C_1$-$C_{20}$-alkyl, preferably $C_1$-$C_4$-alkyl, more preferably methyl, ethyl, n-propyl, isopropyl, n-butyl, isobutyl, sec-butyl or tert-butyl, substituted or unsubstituted $C_6$-$C_{30}$-aryl, preferably substituted or unsubstituted phenyl, more preferably unsubstituted phenyl, tolyl, dimethylphenyl, trimethylphenyl, F-, CN-, methoxy- and/or $CF_3$-substituted phenyl, substituted or unsubstituted heteroaryl having from 5 to 30 ring atoms, preferably substituted or unsubstituted heteroaryl having from 5 to 13 ring atoms, more preferably pyridyl, thienyl, pyrrolyl, furyl, thiazolyl, oxazolyl, pyrazolyl or imidazolyl, $C_1$-$C_{20}$-alkoxy, preferably $C_1$-$C_4$-alkoxy, more preferably methoxy, $C_6$-$C_{30}$-aryloxy, preferably $C_6$-$C_{10}$-aryloxy, more preferably phenoxy, $C_1$-$C_{20}$-alkylthio, preferably $C_1$-$C_4$-alkylthio, more preferably $SCH_3$, $C_6$-$C_{30}$-arylthio, preferably $C_6$-$C_{10}$-arylthio, more preferably SPh, $SiR^4R^5R^6$, preferably $SiMe_3$ or $SiPh_3$, halogen radicals, preferably F, Cl, Br, more preferably F, halogenated $C_1$-$C_{20}$-alkyl radicals, preferably halogenated $C_1$-$C_{10}$-alkyl radicals, more preferably $CF_3$, and pseudohalogen radicals, preferably CN;

or two adjacent $R^3$ radicals together form a saturated or unsaturated, methyl-, phenyl-, methoxy-, $SiMe_3$-, $SiPh_3$-, F-, $CF_3$- or CN-substituted or unsubstituted bridge composed of 3 or 4 carbon atoms, such that the $R^3$ radicals together with one of the elements A=D, D-E, A'=D', D'-E', E'=G' form a 5- or 6-membered ring;

or the $R^3$ radicals at the G' and A positions together form a saturated or unsaturated, methyl-, phenyl-, methoxy-, $SiMe_3$-, $SiPh_3$-, F-, $CF_3$- or CN-substituted or unsubstituted bridge composed of 1 or 2 carbon atoms, such that the $R^3$ radicals together with the element -G'-C—C-A- form a 5- or 6-membered ring.

In a particularly preferred embodiment, $R^1$ (if the $R^1$ radical is present) and $R^3$ are each as defined above for $R^1$ and $R^3$ and $R^2$ is selected from the group consisting of substituted or unsubstituted $C_1$-$C_{20}$-alkyl which is branched in the 1-position, preferably isopropyl, isobutyl, isopentyl, sec-butyl or tert-butyl; substituted or unsubstituted $C_6$-aryl, preferably unsubstituted phenyl or phenyl which is substituted in the 2- and/or 6-position, preferably by methyl, methoxy, $CF_3$, CN and/or F; more preferably 2-tolyl, 2-methoxyphenyl, 2-cyanophenyl, 2-trifluoromethylphenyl, 2,6-difluorophenyl, 2,3-, 2,4-, 2,5- or 2,6-dimethylphenyl or 2,4,6-, 2,3,4- or 2,3,5-trimethylphenyl; substituted or unsubstituted heteroaryl having from 5 to 13 ring atoms, preferably pyridin-2-yl, pyridin-3-yl, pyridin-4-yl, thiophen-2-yl, thiophen-3-yl, pyrrol-2-yl, pyrrol-3-yl, furan-2-yl, furan-3-yl, thiazol-2-yl, oxazol-2-yl, pyrazol-3-yl or imidazol-2-yl, and the corresponding benzofused radicals.

It has been found that carbene complexes of the formula I which have the aforementioned particularly preferred $R^2$ radicals have particularly good stability.

In a preferred embodiment, the present invention relates to bridged cyclometalated carbene complexes of the formula I in which X is N.Y. is preferably $NR^2$ where suitable $R^2$ radicals are as defined above. Particular preference is thus given to carbene complexes of the formula I in which:

X is N, and
Y is $NR^2$
where $R^2$ is as defined above.

The A, D, G, E, A', D', G' and E' groups in the carbene complexes of the formula I are each independently CH, $CR^3$ or N. Preferably 0, 1 or 2 groups, more preferably 0 or 1 group, selected from the A, D, G and E groups or selected from the A', D', G' and E' groups, is/are N. In a particularly preferred embodiment, the A, D, G, E, A', D', G' and E' groups are each CH or $CR^3$, most preferably CH. Suitable $R^3$ radicals are specified above.

Particularly preferred carbene complexes of the formula I are selected from carbene complexes of the formulae Ia and Ib:

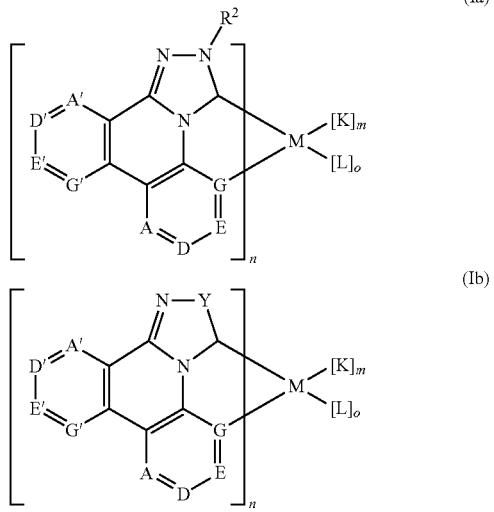

in which:

A, D, G, E, A', D', G' and E'
are each independently CH, $CR^3$ or N, preferably CH or $CR^3$, more preferably CH;

$R^2$, $R^3$ are each independently substituted or unsubstituted $C_1$-$C_{20}$-alkyl, substituted or unsubstituted $C_5$-$C_{20}$-cycloalkyl, substituted or unsubstituted $C_5$-$C_{20}$-cycloalkenyl, substituted or unsubstituted heterocycloalkyl having from 5 to 30 ring atoms, substituted or unsubstituted heterocycloalkenyl having from 5 to 30 ring atoms, substituted or unsubstituted $C_2$-$C_{20}$-alkenyl, substituted or unsubstituted $C_2$-$C_{20}$-alkynyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals, carbonyl (—CO($R^4$)), carbonylthio (—C=O(S$R^4$)), carbonyloxy (—C=O(O$R^4$)), oxycarbonyl (—OC=O($R^4$)), thiocarbonyl (—SC=O($R^4$)), amino (—N$R^4R^5$), OH, pseudohalogen radicals, amido (—C=O(N$R^4R^5$)), —N$R^4$C=O($R^5$), phosphonate (—P(O)(O$R^4$)$_2$), phosphate (—OP(O)(O$R^4$)$_2$), phosphine (—P$R^4R^5$), phosphine oxide (—P(O)$R^4_2$), sulfate (–OS(O)$_2$O$R^4$), sulfoxide (—S(O)$R^4$), sulfonate (—S(O)$_2$O$R^4$), sulfonyl (—S(O)$_2R^4$), sulfonamide (—S(O)$_2$N$R^4R^5$), NO$_2$, boronic esters (—B(O$R^4$)$_2$), imino (—C=N$R^4R^5$), borane radicals, stannate radicals, hydrazine radicals, hydrazone radicals, oxime radicals, nitroso groups, diazo groups, vinyl groups, sulfoximines, alanes, germanes, boroxines and borazines;
or
two adjacent $R^3$ radicals together form a saturated or unsaturated, substituted or unsubstituted bridge composed of from 3 to 6 atoms, such that the $R^3$ radicals together with one of the elements A=D, D-E, A'=D', D'-E', E'=G' form a 5- to 8-membered ring;
or
the $R^3$ radicals at the G' and A positions together form a saturated or unsaturated, substituted or unsubstituted bridge composed of from 1 to 4 atoms, such that the $R^3$ radicals together with the element -G'-C—C-A- form a 5- to 8-membered ring;
where $R^2$ is preferably selected from the group consisting of substituted or unsubstituted $C_1$-$C_{20}$-alkyl which is branched in the 1-position, preferably isopropyl, isobutyl, isopentyl, sec-butyl or tert-butyl; substituted or unsubstituted $C_6$-aryl, preferably unsubstituted phenyl or phenyl which is substituted in the 2- and/or 6-position, preferably by methyl, methoxy, $CF_3$, CN and/or F; more preferably 2-tolyl, 2-methoxyphenyl, 2-cyanophenyl, 2-trifluoromethylphenyl, 2,6-difluorophenyl, 2,3-, 2,4-, 2,5- or 2,6-dimethylphenyl or 2,4,6-, 2,3,4- or 2,3,5-trimethylphenyl; substituted or unsubstituted heteroaryl having from 5 to 13 ring atoms, preferably pyridin-2-yl, pyridin-3-yl, pyridin-4-yl, thiophen-2-yl, thiophen-3-yl, pyrrol-2-yl, pyrrol-3-yl, furan-2-yl, furan-3-yl, thiazol-2-yl, oxazol-2-yl, pyrazol-3-yl or imidazol-2-yl, and the corresponding benzofused radicals;

$R^4$, $R^5$, $R^6$
are each independently H, substituted or unsubstituted $C_1$-$C_{20}$-alkyl or substituted or unsubstituted $C_6$-$C_{30}$-aryl, or substituted or unsubstituted heteroaryl having from 5 to 30 ring atoms;

Y is $CR^2_2$;
M is Ir, Os or Pt; preferably Ir(III), Os(II) or Pt(II), more preferably Ir(III);

K is an uncharged bidentate ligand;

L is a monoanionic bidentate ligand;

n is the number of carbene ligands, where n is 3 in the case of Ir, is 2 in the case of Os and is 1 or 2 in the case of Pt, and the carbene ligands in the complexes of the formulae Ia, Ib, Ic and Id may be the same or different;

m is 0 in the case that M=Ir or Pt and is 1 in the case of Os;

o is 0 in the case that M=Ir or Os and Pt and in the case that n=2, and is 1 in the case of Pt and in the case that n=1.

Particularly preferred radicals, groups and indices M, $R^2$, $R^3$, $R^4$, $R^5$, $R^6$, A, D, G, E, A', D', G', E', Y, M, K, L, n, m and o are specified above. Most preferably, M in the carbene complexes of the formulae Ia, Ib, Ic and Id is Ir(III), n is 3 and m and o are each 0.

Very particular preference is given to carbene complexes of the formulae specified below:

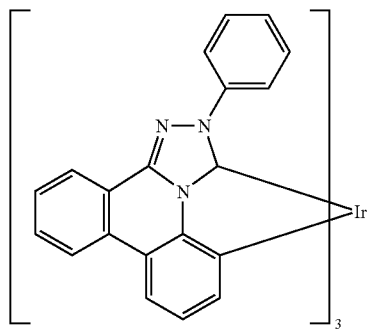

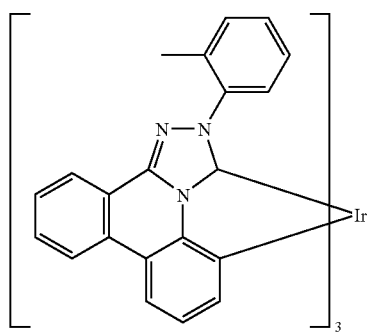

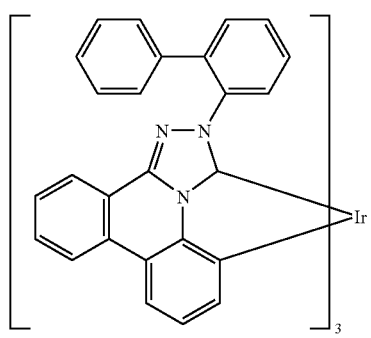

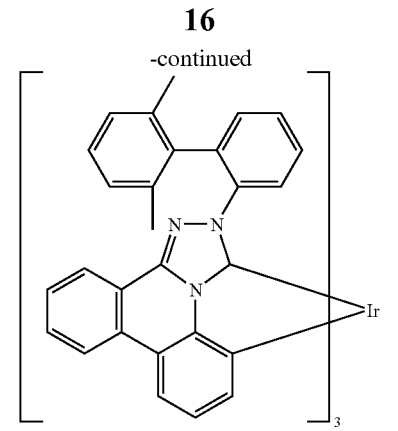

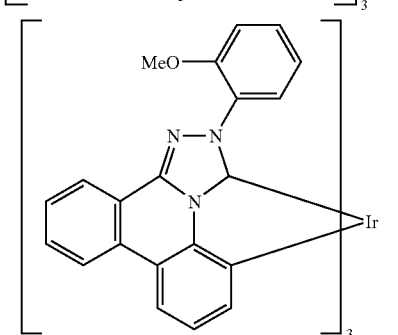

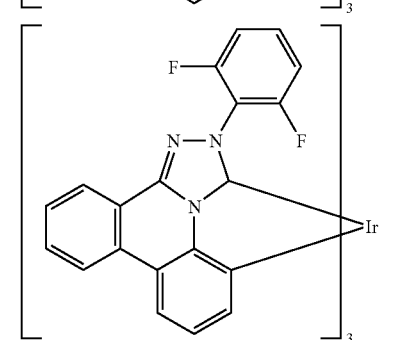

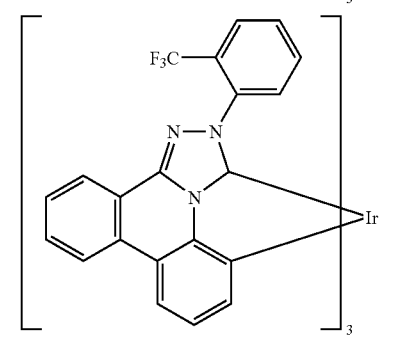

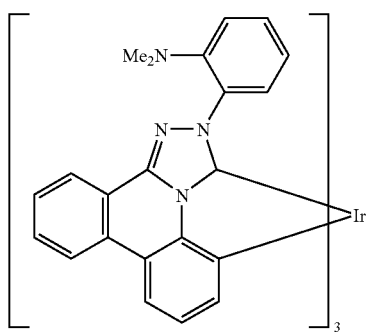
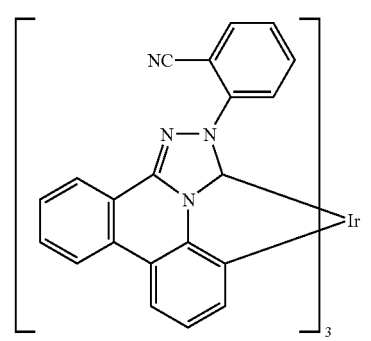
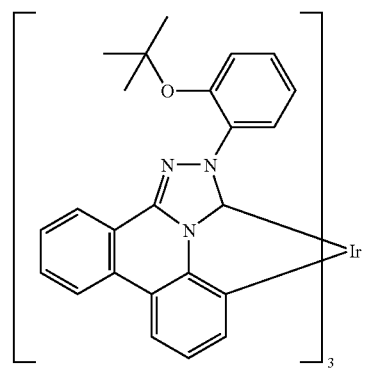
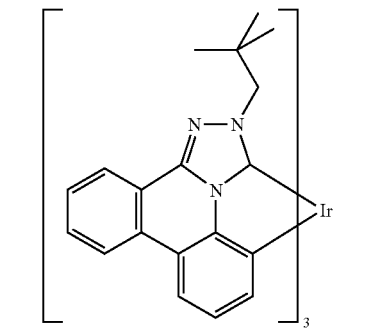
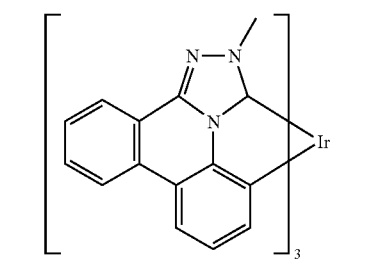
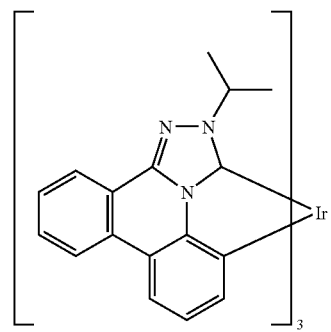
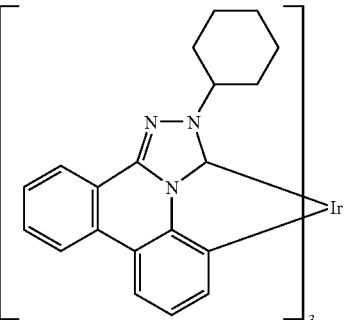
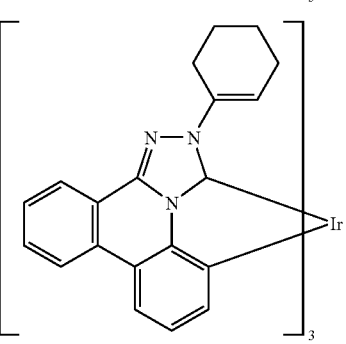
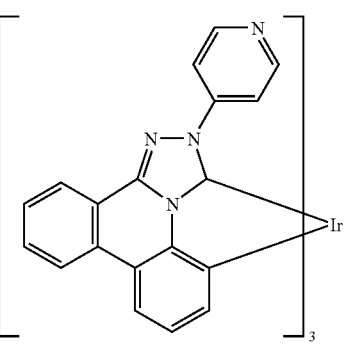
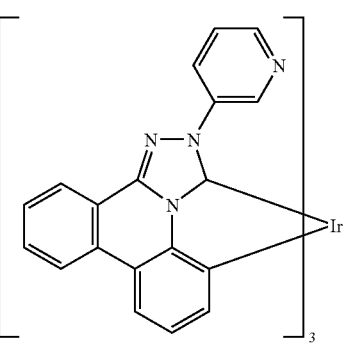

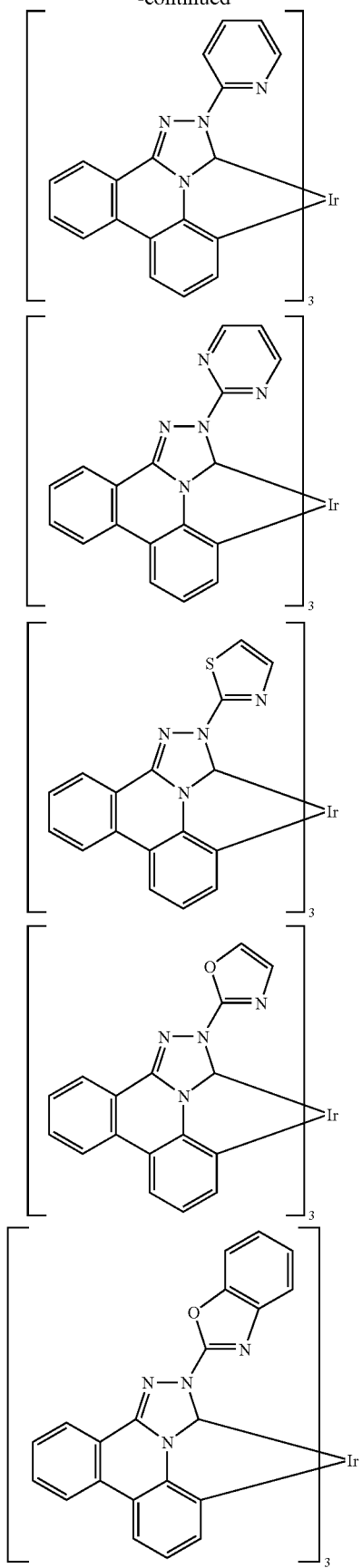
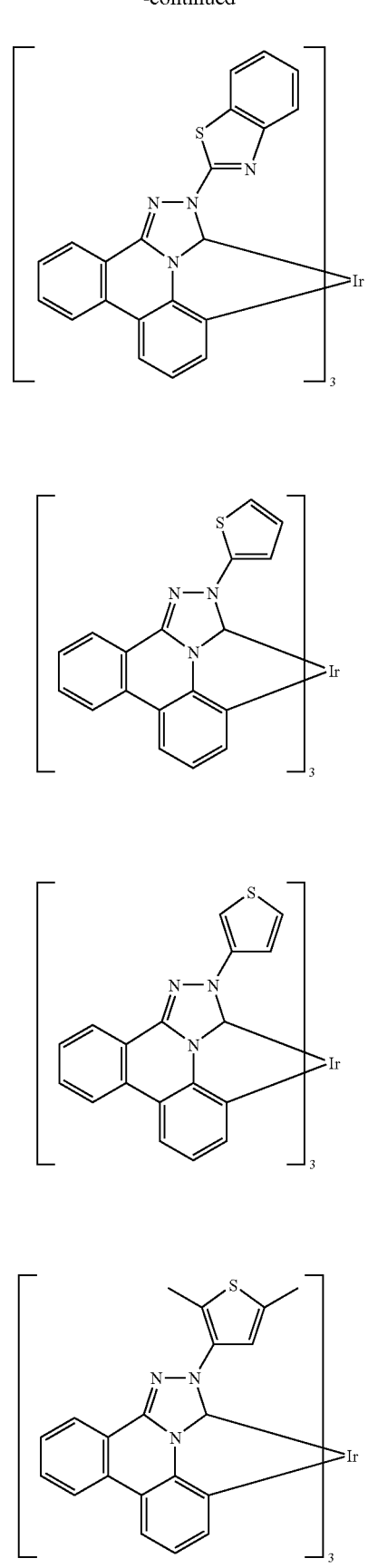

21
-continued
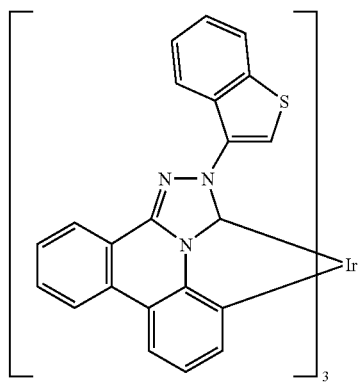
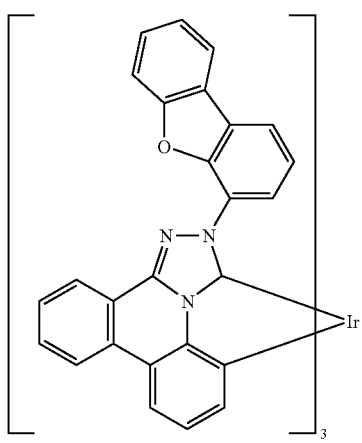
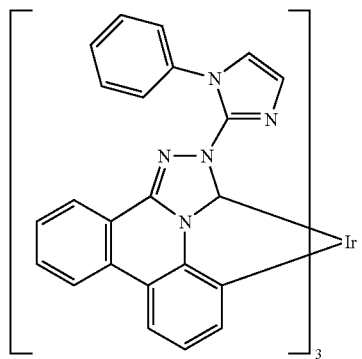
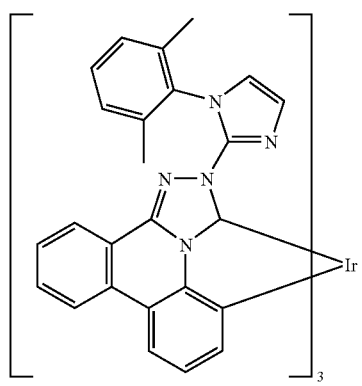
22
-continued
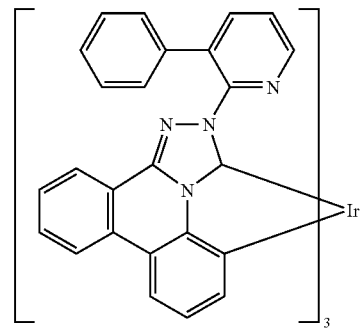
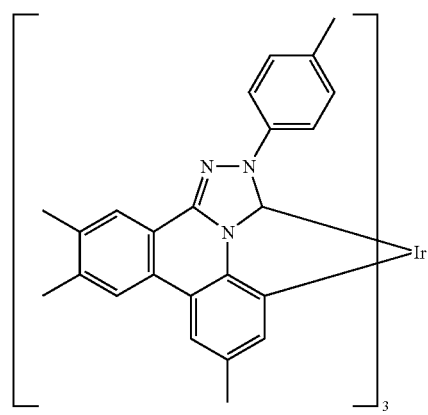
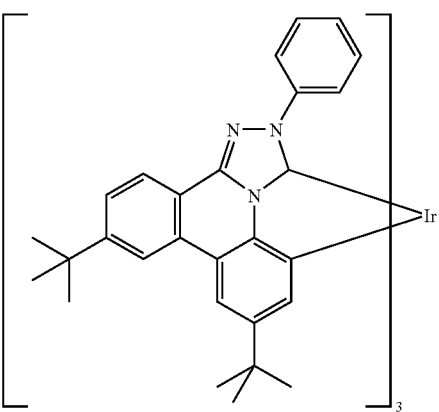
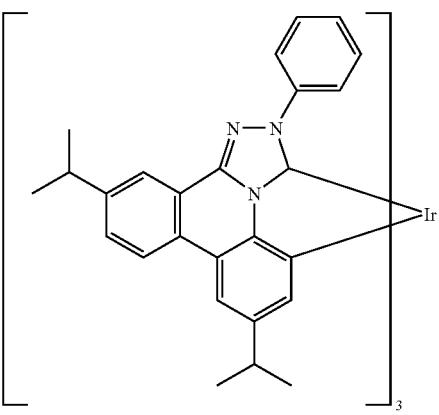

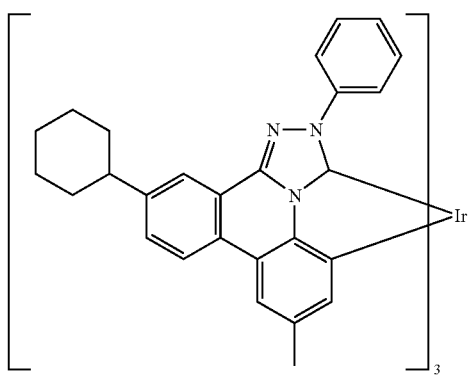
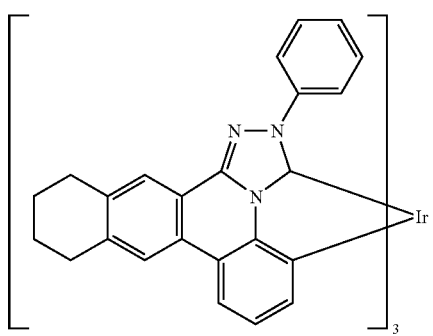
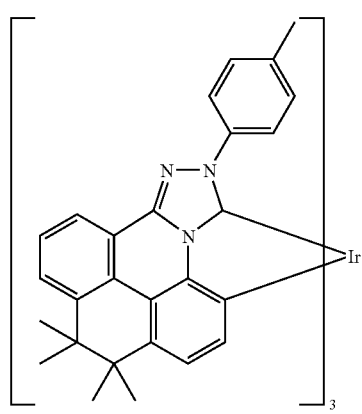
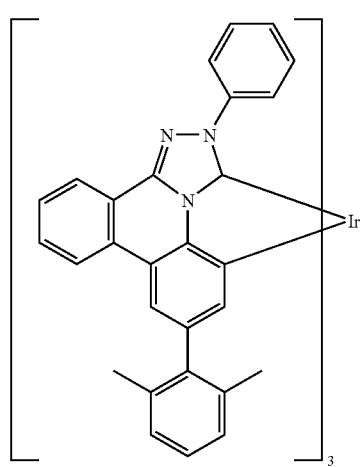
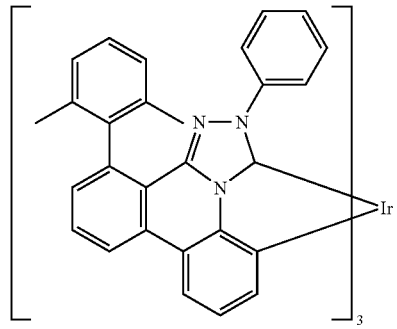
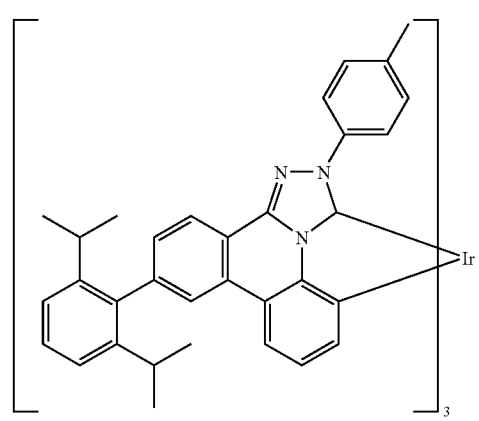
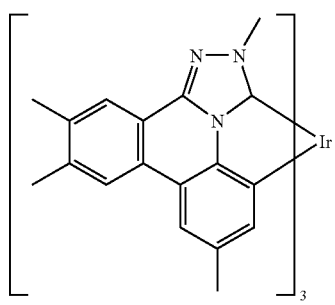
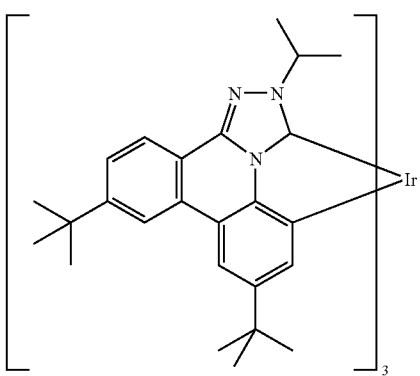

-continued
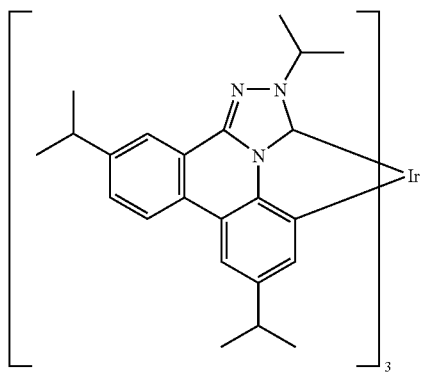
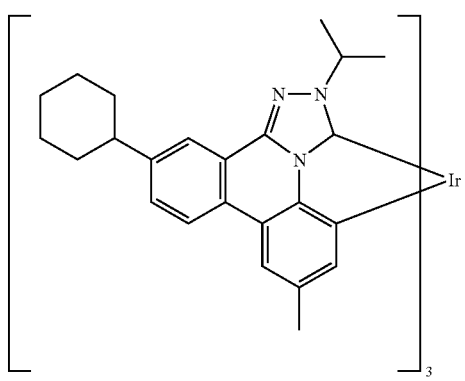
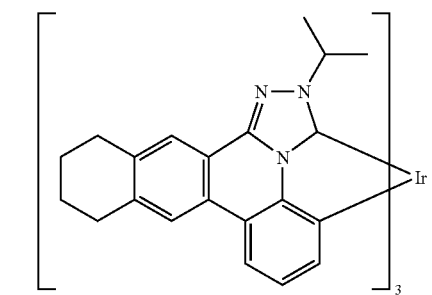
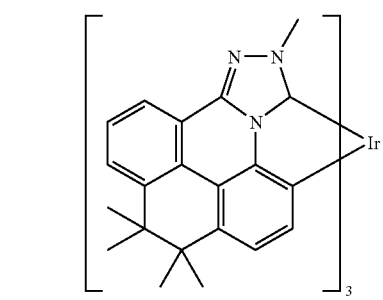
-continued
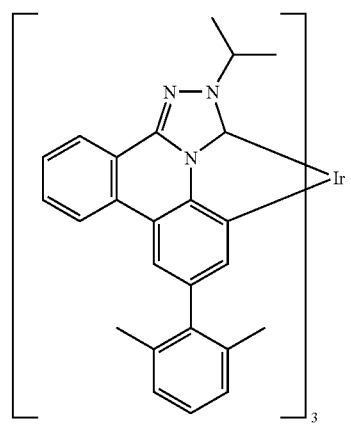
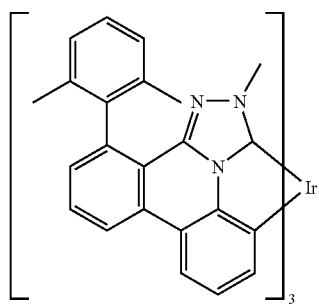
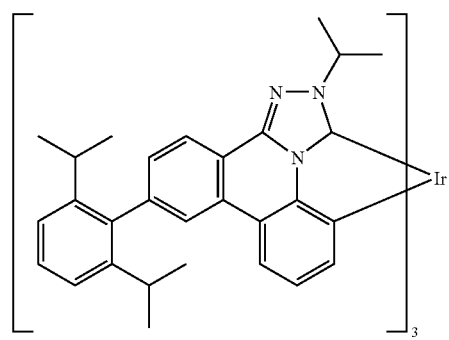
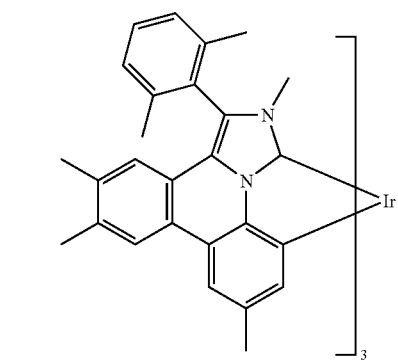

-continued
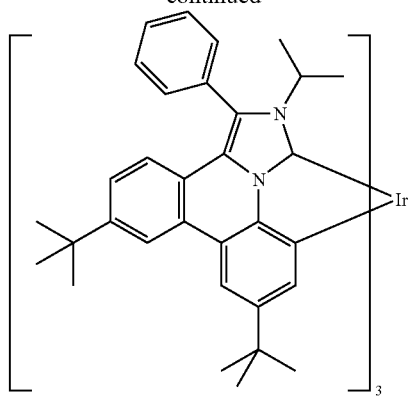
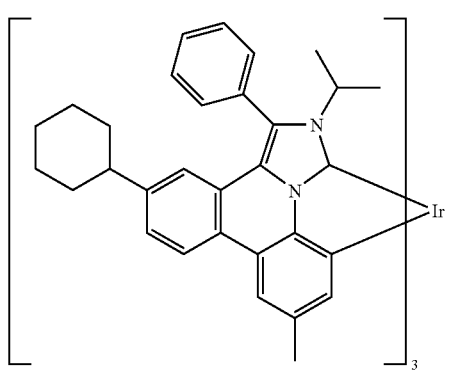
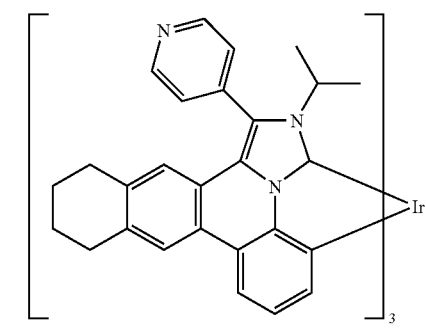
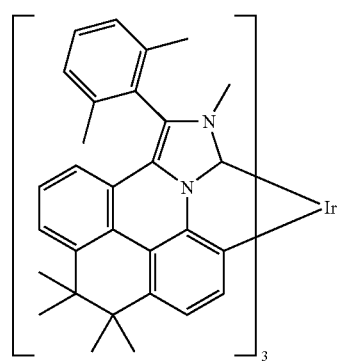
-continued
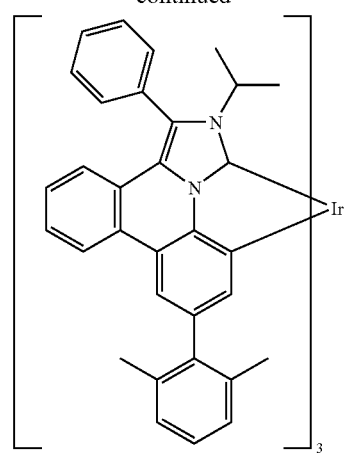
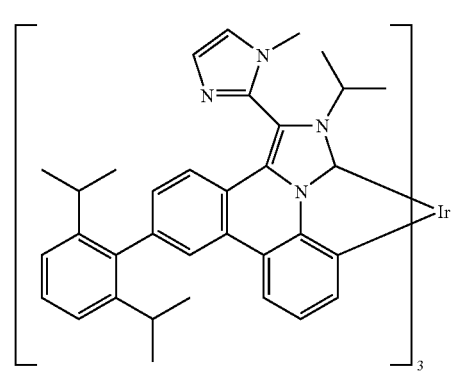
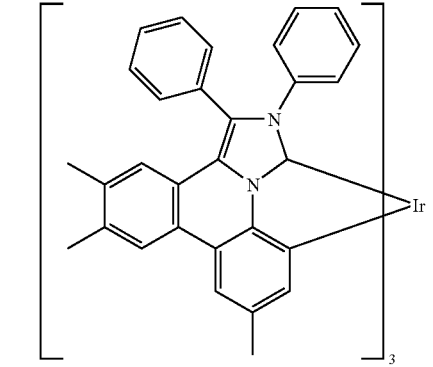
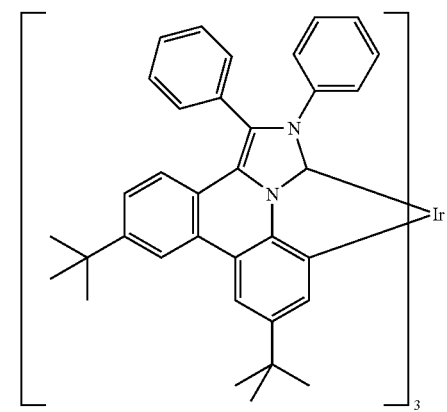

-continued

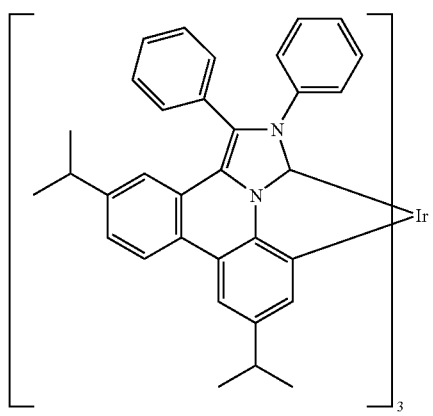

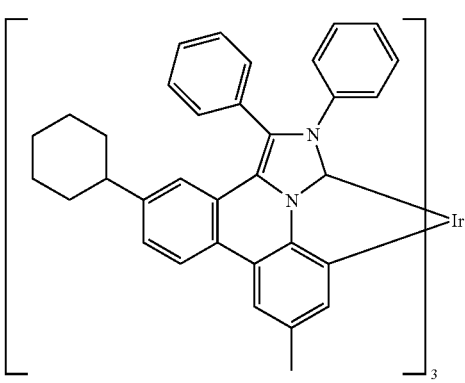

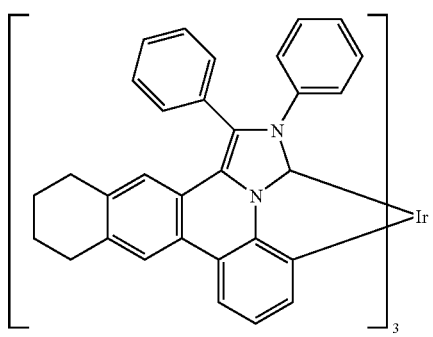

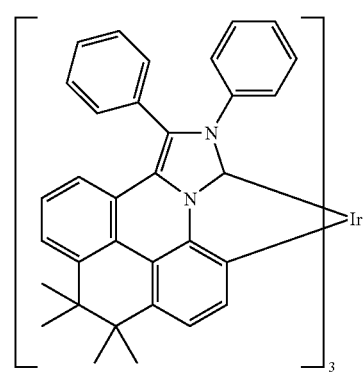

-continued

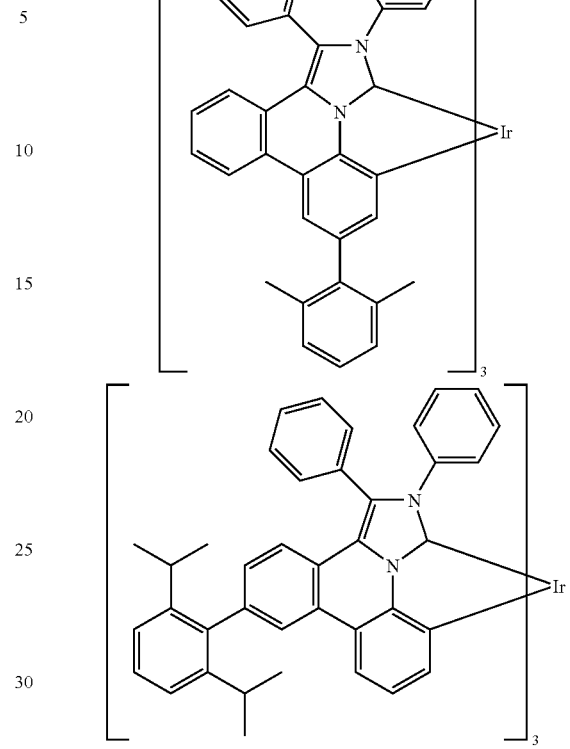

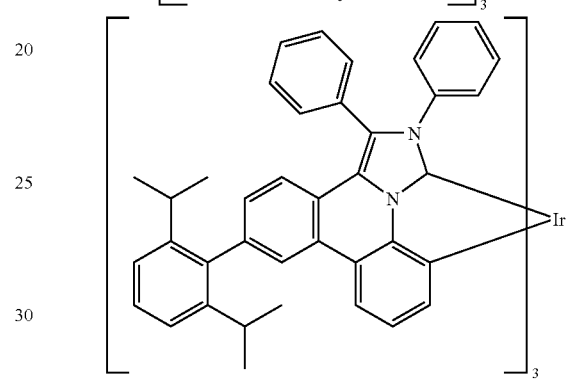

The aforementioned compounds may optionally be substituted by one or more further substituents according to the definition of the general formula I.

The inventive bridged cyclometalated carbene complexes of the formula I can in principle be prepared analogously to processes known to those skilled in the art. Suitable processes for preparing carbene complexes are detailed, for example, in the review articles W. A. Hermann et al., Advances in Organometallic Chemistry, 2001 vol. 48, 1 to 69, W. A. Hermann et al., Angew. Chem. 1997, 109, 2256 to 2282 and G. Bertrand et al. Chem. Rev. 2000, 100, 39 to 91 and the literature cited therein, and also in WO 2005/113704, WO 2005/019373 and WO 2007/088093.

In one embodiment, the inventive bridged cyclometalated carbene complexes of the formula I are prepared from ligand precursors corresponding to the carbene ligands and suitable metax complexes comprising the desired metal.

Suitable ligand precursors of the carbene ligands are known to those skilled in the art. They are preferably cationic precursors of the carbene ligands of the general formula III

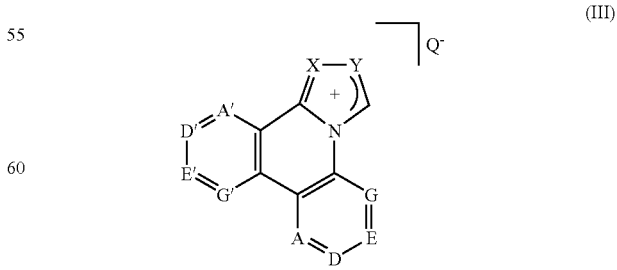

(III)

in which $Q^-$ is a monoanionic counterion, preferably halide, pseudohalide, $BF_4^-$, $BPh_4^-$, $PF_6^-$, $AsF_6^-$ or $SbF_6^-$;

and
the further radicals, symbols and indices are each as defined above in the ligand precursor of the general formula III.

The ligand precursors of the general formula III can be prepared analogously to processes known to those skilled in the art. Suitable processes are specified, for example, in WO 2005/019373 and the literature cited therein, for example Organic Letters, 1999, 1, 953-956; Angewandte Chemie, 2000, 112, 1672-1674. Further suitable processes are specified, for example, in T. Weskamp et al., J. Organometal. Chem. 2000, 600, 12-22; G. Xu et al., Org. Lett. 2005, 7, 4605-4608; V. Lavallo et al., Angew. Chem. Int. Ed. 2005, 44, 5705-5709.

In a preferred embodiment, the present invention relates to a process for preparing the inventive cyclometalated bridged carbene complexes of the general formula I, wherein the preparation comprises the following step:

Reaction of at least one ligand precursor of the general formula (III)

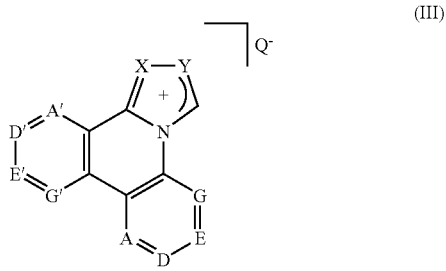

(III)

in which
$Q^-$ is a monoanionic counterion, preferably halide, pseudohalide, $BF_4^-$, $BPh_4^-$, $PF_6^-$, $AsF_6^-$ or $SbF_6^-$;
and
the further symbols in the ligand precursor of the general formula III are each defined as follows:
X is $CR^1$ or N, preferably N;
Y is $NR^2$ or $CR^2_2$;
A, D, G, E, A', D', G' or E'
  are each independently CH, $CR^3$ or N;
$R^1$ is F, CN, $C_1$-$C_{20}$-alkoxy, $C_6$-$C_{30}$-aryloxy, $C_1$-$C_{20}$-alkylthio, $C_6$-$C_{30}$-arylthio, substituted or unsubstituted $C_6$-$C_{30}$-aryl or substituted or unsubstituted heteroaryl having from 5 to 30 ring atoms;
$R^2$, $R^3$
  are each independently substituted or unsubstituted $C_1$-$C_{20}$-alkyl, substituted or unsubstituted $C_5$-$C_{20}$-cycloalkyl, substituted or unsubstituted $C_5$-$C_{20}$-cycloalkenyl, substituted or unsubstituted heterocycloalkyl having from 5 to 30 ring atoms, substituted or unsubstituted heterocycloalkenyl having from 5 to 30 ring atoms, substituted or unsubstituted $C_2$-$C_{20}$-alkenyl, substituted or unsubstituted $C_2$-$C_{20}$-alkynyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals, carbonyl (—CO($R^4$)), carbonylthio (—C=O($SR^4$)), carbonyloxy (—C=O($OR^4$)), oxycarbonyl (—OC=O($R^4$)), thiocarbonyl (—SC=O($R^4$)), amino (—$NR^4R^5$), OH, pseudohalogen radicals, amido (—C=O($NR^4R^5$)), —$NR^4$C=O($R^5$), phosphonate (—P(O)($OR^4$)$_2$), phosphate (—OP(O)($OR^4$)$_2$), phosphine (—$PR^4R^5$), phosphine oxide (—P(O)$R^4_2$), sulfate (—OS(O)$_2OR^4$), sulfoxide (—S(O)$R^4$), sulfonate (—S(O)$_2OR^4$), sulfonyl (—S(O)$_2R^4$), sulfonamide (—S(O)$_2NR^4R^5$), $NO_2$, boronic esters (—B($OR^4$)$_2$), imino (—C=$NR^4R^5$), borane radicals, stannate radicals, hydrazine radicals, hydrazone radicals, oxime radicals, nitroso groups, diazo groups, vinyl groups, sulfoximines, alanes, germanes, boroxines and borazines;
or
two adjacent $R^3$ radicals together form a saturated or unsaturated, substituted or unsubstituted bridge composed of from 3 to 6 atoms, such that the $R^3$ radicals together with one of the elements A=D, D-E, A'=D', D'-E', E'=G' form a 5- to 8-membered ring;
or
the $R^3$ radicals at the G' and A positions together form a saturated or unsaturated, substituted or unsubstituted bridge composed of from 1 to 4 atoms, such that the $R^3$ radicals together with the element -G'-C=C-A- form a 5- to 8-membered ring; and
$R^4$, $R^5$, $R^6$
  are each independently H, substituted or unsubstituted $C_1$-$C_{20}$-alkyl or substituted or unsubstituted $C_6$-$C_{30}$-aryl or substituted or unsubstituted heteroaryl having from 5 to 30 ring atoms;
with a metal complex comprising at least one metal M where M is defined as follows:
M is a metal atom selected from the group consisting of metals of group IB, IIB, IIIB, IVB, VB, VIIB, VIIB, VIIIB, the lanthanides and IIIA of the Periodic Table of the Elements (CAS version) in any oxidation state possible for the appropriate metal atom; preferably Fe, Os, Co, Rh, Ir, Ni, Ru, Pd and Pt, Cu, Au, Ce, Tb, Eu, more preferably Os, Ru, Rh, Ir and Pt and most preferably Ir, Os and Pt.

Particularly preferred radicals, groups and indices M, $R^2$, $R^3$, $R^4$, $R^5$, $R^6$, A, D, G, E, A', D', G', E', Y, M, K, L, n, m and o have been specified above.

If appropriate, the inventive reaction of the ligand precursors of the formula III with the metal complex is effected in the presence of suitable ligand precursors of the ligands K and/or L ("one-pot process") if m and/or o is not 0 in the carbene complexes of the formula I. Suitable ligand precursors of ligands K and L are known to those skilled in the art. Or, if m and/or o is not 0, a sequential reaction is effected. The sequential reaction can be effected either by reacting the metal complex with at least one carbene ligand precursor of the general formula III in a first step, in which case a carbene complex which has at least one carbene ligand in cyclometalated or non-cyclometalated form and has at least one further coordination means (in which case the further coordination means is present either through a free coordination site on the metal M or through the displacement of other ligands) for at least one further bidentate ligand K and/or L is initially prepared as an intermediate; or by reacting the metal complex with at least one ligand precursor for the ligands K and/or L in a first step, in which case a complex which has at least one ligand K and/or L and at least one further coordination means (in which case the further coordination means is present either through a free coordination site on the metal M' or through the displacement of other ligands) for at least one bidentate carbene ligand is initially prepared as an intermediate. In a second step, which follows the first step, the particular complex obtained in the first step is reacted with at least one ligand precursor of the ligands K and/or L (when at least one carbene ligand precursor has been used in the first step), or with at least one carbene ligand precursor of the general formula III (when at least one ligand precursor of the ligands K and/or L was used in the first step).

In the particularly preferred case that the metal M in the inventive carbene complexes of the formula I is Ir(III) with a coordination number of 6 and n=3 and m and o are each 0, a reaction is effected with one carbene ligand precursor or different carbene ligand precursors of the formula III. When different carbene ligand precursors of the formula III are used, the reaction can be effected in the form of a "one-pot reaction" or sequentially—as described above using a carbene ligand precursor and ligand precursors for the ligands K and L. The carbene ligands in the carbene complex of the formula I are preferably identical, such that a reaction of the carbene ligand precursor of the formula III is effected with a suitable metal complex.

For the very particularly preferred case (M=Ir(III), n=3), the metal:ligand precursor stoichiometry is generally from 1:3 to 1:9, preferably from 1:3 to 1:6.

In the case that a carbene ligand is present in the inventive carbene complexes of the formula I and the metal atom is Ir(III) (M=Ir(III), n=1), the metal:ligand precursor stoichiometry is generally from 1:1 to 1:3, preferably from 1:1 to 1:2.

The metal complex comprising at least one metal M is a metal complex comprising at least one metal selected from the group consisting of metals of group IB, IIB, IIIB, IVB, VB, VIIB, VIIB, VIIIB, the lanthanides and IIIA of the Periodic Table of the Elements (CAS version) in any oxidation state possible for the appropriate metal atom; preferably Fe, Os, Co, Rh, Ir, Ni, Ru, Pd and Pt, Cu, Au, Ce, Tb, Eu, more preferably Os, Ru, Rh, Ir and Pt and most preferably Ir, Os and Pt. Preference is given to using Pt(II), Os(II), Ir(I) or Ir(III) in the metal complexes used in the process according to the invention, particular preference being given to Ir(I) and Ir(III) and very particular preference to NI). Suitable metal complexes are known to those skilled in the art. Examples of suitable metal complexes are Pt(cod)Cl$_2$, Pt(cod)Me$_2$, Pt(acac)$_2$, Pt(PPh$_3$)$_2$Cl$_2$, PtCl$_2$, [Rh(cod)Cl]$_2$, Rh(acac)CO (PPh$_3$), Rh(acac)(CO)$_2$, Rh(cod)$_2$BF$_4$, RhCl(PPh$_3$)$_3$, RhCl$_3$× H$_2$O, Rh(acac)$_3$, [Os(CO)$_3$I$_2$]$_2$, [Os$_3$(CO)$_{12}$], OsH$_4$(PPh$_3$)$_3$, Cp$_2$Os, Cp*$_2$Os, H$_2$OsCl$_6$×6H$_2$O, OsCl$_3$×H$_2$O), and [(μ-Cl)Ir(η$^4$-1,5-cod)]$_2$, [(μ-Cl)Ir(η$^2$-coe)$_2$]$_2$, Ir(acac)$_3$, IrCl$_3$×n H$_2$O, (tht)$_3$IrCl$_3$, Ir(η$^3$-allyl)$_3$, Ir(η$^3$-methallyl)$_3$, in which cod is cyclooctadiene, coe is cyclooctene, acac is acetylacetonate and tht is tetrahydrothiophene. The metal complexes can be prepared by processes known to those skilled in the art or are commercially available.

In the case of preparation of iridium(III) complexes of the general formula I (M in formula I is Ir), which are particularly preferred according to the present application, the aforementioned iridium(I) or (III) complexes can be used, especially [(μ-Cl)Ir(η$^4$-1,5-cod)]$_2$, [(μ-Cl)Ir(η$^2$-coe)$_2$]$_2$, Ir(acac)$_3$, IrCl$_3$×n H$_2$O, (tht)$_3$IrCl$_3$, Ir(η$^3$-allyl)$_3$, Ir(η$^3$-methallyl)$_3$, very particular preference being given to using [(β-Cl)Ir(η$^4$-1,5-cod)]$_2$, in which cod is cyclooctadiene, coe is cyclooctene, acac is acetylacetonate and tht is tetrahydrothiophene.

Particular preference is given to effecting the inventive reaction of the carbene ligand precursor of the formula III with the suitable metal complex in the presence of a base and of an auxiliary reagent or of a basic auxiliary reagent, in which case the basic auxiliary reagent or the auxiliary reagent comprises at least one metal selected from the group consisting of Ag, Hg, Sb, Mg, B and Al; preference is given to effecting the inventive reaction in the presence of Ag$_2$O. A suitable process which can be employed correspondingly for the preparation of the inventive carbene complexes of the formula I is, for example, disclosed in WO 2007/088093.

In the case that Y is NR$^2$, the suitable ligand precursors of the formula III are prepared, for example, proceeding from ligand precursors of the formula IVa by alkylation, for example by methylation with MeI or Me$_3$OBF$_4$, or proceeding from ligand precursors of the formula IVb by cyclization, for example with CH(OEt)$_3$.

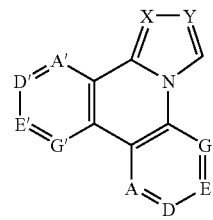

(IVa)

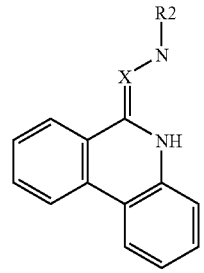

(IVb)

in which the symbols are each as defined above.

Other processes for preparing the ligand precursors of the formula III in which Y is NR$^2$ are also possible, as shown by way of example hereinafter.

The compounds of the formulae IVa and IVb can be prepared by processes known to those skilled in the art, suitable processes being mentioned in the literature specified hereinafter.

Preparation processes for preparing very particularly preferred inventive carbene complexes of the formula I are illustrated by way of example hereinafter, the examples below comprising the preparation of suitable compounds of the formulae IVa and IVb and the preparation of suitable ligand precursors of the formula III proceeding from commercially available compounds or those preparable by processes known to those skilled in the art. The compounds specified in the examples below are illustrative and may be substituted according to the substitution pattern of the compounds of the formula I and/or have heteroatoms in their ring systems according to the compounds of the formula I.

Synthesis of a triazolophenanthridine-based complex 2-alkyl from 1,2,4-triazolo-[4,3-f]phenanthridine (A. G. Mikhailovskii, V. S. Shklyaev, Chem. Heterocycl. Comp. 1992, 445):

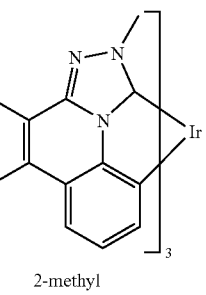
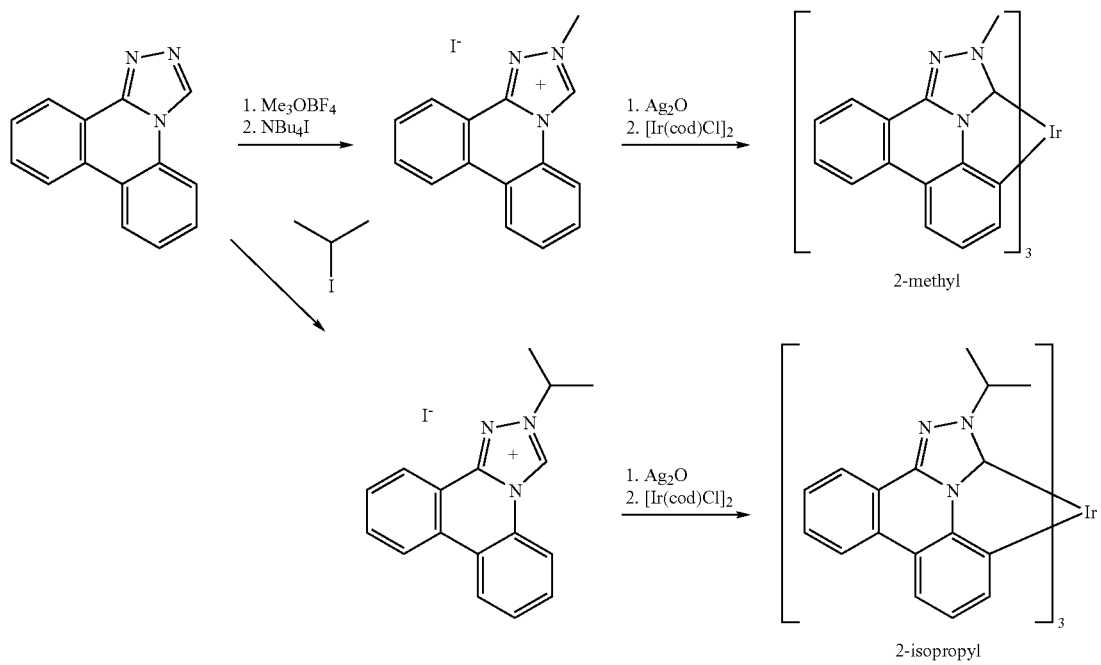

2-methyl

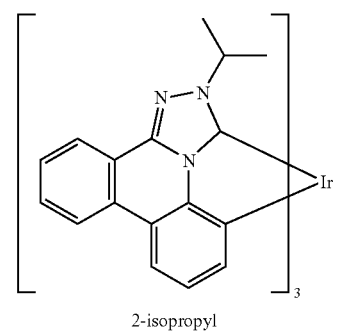

2-isopropyl

Synthesis of triazolophenanthridine-based complexes 2-aryl from 6-chlorophenanthridine (A. G. Mikhailovskii, V. S. Shklyaev, *Chem. Heterocycl. Comp.* 1992, 445):

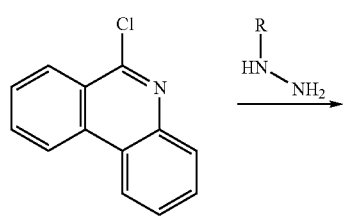

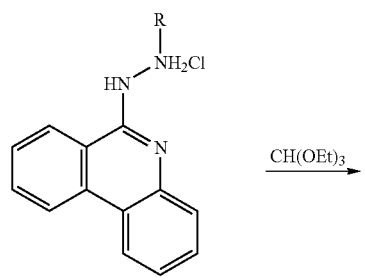

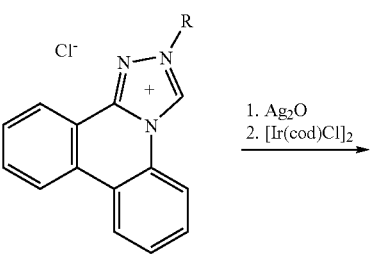

-continued

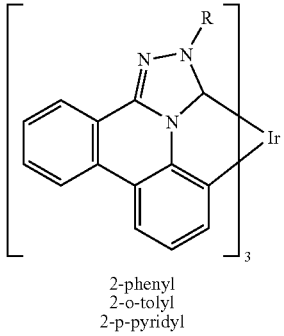

2-phenyl
2-o-tolyl
2-p-pyridyl

R = phenyl, o-tolyl, p-pyridyl

After the reaction, the inventive cyclometalated bridged carbene complex of the formula I is worked up and, if appropriate, purified by processes known to those skilled in the art. Typically, the workup and purification are effected by extraction, column chromatography and/or recrystallization by processes known to those skilled in the art.

The inventive cyclometalated bridged carbene complexes of the formula I are outstandingly suitable as phosphorescent emitter substances, since they have emission (electroluminescence) in the visible region of the electromagnetic spectrum, preferably in the blue region of the electromagnetic spectrum. With the aid of the inventive carbene complexes of the formula I as emitter substances, it is possible to provide compounds which exhibit electroluminescence of good efficiency, the inventive carbene complexes being notable for good stability in the device. At the same time, the quantum yield is high.

In addition, the inventive carbene complexes of the formula I are suitable as electron blockers, exciton blockers or hole blockers or hole conductors, electron conductors, hole injection layer or matrix material in OLEDs, generally depending on the ligands used and the central metal used.

The present invention therefore further provides for the use of the inventive cyclometalated bridged carbene complexes of the formula I in organic light-emitting diodes, preferably as emitter material, matrix material, charge blocker material and/or charge transport material, more preferably as emitter material, most preferably as a blue emitter.

Organic light-emitting diodes (OLEDs) are in principle formed from several layers, for example:
1. Anode (1)
2. Hole-transporting layer (2)
3. Light-emitting layer (3)
4. Electron-transporting layer (4)
5. Cathode (5)

However, it is also possible that the OLED does not have all of the layers mentioned; for example, an OLED with layers (1) (anode), (3) (light-emitting layer) and (5) (cathode) is likewise suitable, in which case the functions of layers (2) (hole-transporting layer) and (4) (electron-transporting layer) are assumed by the adjacent layers. OLEDs which have layers (1), (2), (3) and (5) or layers (1), (3), (4) and (5) are likewise suitable.

The inventive cyclometalated bridged carbene complexes of the formula I can be used in different layers of an OLED. A carbene complex of the formula I can be used in one layer of an OLED, but it is likewise possible that two or more different carbene complexes of the formula I are used in one or more layers of the OLED. For example, both the emitter material and the matrix material in the light-emitting layer of the OLED may comprise a carbene complex of the formula I, in which case the carbene complex of the formula I used as the emitter material and that used as the matrix material are generally different. It is likewise possible that the emitter material and the hole conductor material comprise a carbene complex of the formula I, in which case the carbene complexes of the formula I are generally different. Further combinations of different carbene complexes are possible and can be determined by the person skilled in the art. The present invention therefore further provides an OLED comprising at least one inventive cyclometalated bridged carbene complex of the formula I. The inventive cyclometalated bridged carbene complexes of the formula I are preferably used in the light-emitting layer, for example as matrix molecules or emitter molecules, more preferably as emitter molecules. The present invention therefore further provides a light-emitting layer comprising at least one inventive cyclometalated bridged carbene complex of the formula I, preferably as an emitter molecule. Preferred inventive cyclometalated bridged carbene complexes of the formula I have been specified above.

The inventive cyclometalated bridged carbene complexes of the formula I may be present in bulk—without further additives—in the light-emitting layer or another layer of the OLED, preferably in the light-emitting layer. However, it is likewise possible and preferred that, as well as the inventive cyclometalated bridged carbene complexes of the formula I, further compounds are present in the layers comprising at least one inventive cyclometalated bridged carbene complex of the formula I, preferably in the light-emitting layer. For example, a fluorescent dye may be present in the light-emitting layer, in order to change the emission color of the inventive cyclometalated bridged carbene complex of the formula I used as an emitter molecule. In addition—in a preferred embodiment—a diluent material can be used.

This diluent material may be a polymer, for example poly (N-vinylcarbazole) or polysilane. However, the diluent material may likewise be a small molecule, for example 4,4'-N,N'-dicarbazolebiphenyl (CDP=CBP) or tertiary aromatic amines. In addition, the carbene complex of the formula I in the light-emitting layer may be used together with a matrix material, suitable matrix materials being specified below. The use of the inventive carbene complexes of the formula I as a matrix material (together with the use of the carbene complexes of the formula I as an emitter material (in which case the carbene complexes used as the matrix material and emitter material are generally different)) has already been mentioned above.

The individual layers of the OLED among those mentioned above may in turn be formed from 2 or more layers. For example, the hole-transporting layer may be formed from a layer into which holes are injected from the electrode and a layer which transports the holes away from the hole injection layer into the light-emitting layer. The electron-transporting layer may likewise consist of a plurality of layers, for example of a layer in which electrons are injected through the electrode, and a layer which receives electrons from the electron injection layer and transports them into the light-emitting layer. The person skilled in the art is capable of selecting the structure of the OLEDs such that it is adjusted optimally to the inventive carbene complexes of the formula I used in accordance with the invention, preferably as emitter substances.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be formed from any material which is typically used in such layers and is known to those skilled in the art.

Suitable materials for the aforementioned layers (anode, cathode, hole and electron injection materials, hole and electron transport materials, and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, Ed.: Z. Li, H. Meng, Taylor & Francis, 2007, Chapter 3, pages 295 to 411.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for the layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole transport material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]-cyclohexane (TAPC), N,N'-bis(4-methylphenyl)-N,N'-bis(4-ethylphenyl)-[1,1'-(3,3'-dimethyl)-biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4''-tris(N,N-diphenylamino)triphenylamine (TDTA), 4,4',4''-tris(N-3-methyphenyl-N-phenylamino)triphenylamine (m-MTDATA), 2,2,7,7-tetrakis(diphenylamino)-9,9-spirobifluorene (Spiro-TAD), 4,4',4''-tris(carbazol-9-yl)triphenylamine (TCTA) and porphyrin compounds, and also phthalocyanines such as copper phthalocyanines. Customarily used hole-transporting polymers are selected from the group consisting of polyvinylcarbazoles, (phenylmethyl)polysilanes, PEDOT (poly(3,4-ethylenedioxythiophene)), preferably PEDOT doped with PSS (polystyrenesulfonate), and polyanilines. It is likewise possible to obtain hole-transporting polymers by doping hole-transporting molecules into polymers such as polystyrene and polycarbonate. Suitable hole-transporting molecules are the molecules already mentioned above.

Suitable electron transport materials for the layer (4) of the inventive OLEDs comprise metals chelated with oxinoid compounds, such as tris(8-hydroxyquinolato)aluminum ($Alq_3$) or bis(2-methyl-8-quinolato)-(p-phenylphenolato) aluminum (BALq) compounds based on phenanthroline such as 2,9-dimethyl-4,7-diphenyl-1,10-phenanthroline (DDPA=BCP) or 4,7-diphenyl-1,10-phenanthroline (BPhen) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 1,3-bis(4-tert-butylphenyl-1,3,4-oxadiazoyl)phenylene (OXD7), 2,2',2''-(1,3,5-benzenetriyl)-tris(1-phenylbenzimidazole) (TPBI). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

Of the materials specified above as hole transport materials and electron-transporting materials, some can fulfill a plurality of functions. For example, some of the electron-conducting materials are simultaneously hole-blocking materials when they have a low-lying HOMO.

The charge transport layers may also be electronically doped in order to improve the transport properties of the materials used, in order firstly to make the layer thicknesses more generous (avoidance of pinholes/short circuits) and secondly to minimize the operating voltage of the device. For example, the hole transport materials may be doped with electron acceptors; for example, phthalocyanines or arylamines such as TPD or TDTA may be doped with tetrafluorotetracyanoquinodimethane (F4-TCNQ). The electron transport materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo, Appl. Phys. Lett., Vol. 82, No. 25, Jun. 23, 2003 and Pfeiffer et al., Organic Electronics 2003, 4, 89-103 and K. Walzer, B. Maennig, M. Pfeiffer, K. Leo, Chem. Soc. Rev. 2007, 107, 1233.

Suitable matrix materials are in principle the materials mentioned as hole and electron transport materials, and also carbene complexes, for example the carbene complexes of the formula I or the carbene complexes mentioned in WO 2005/019373. Particularly suitable matrix materials are carbazole derivatives, e.g. 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and also the matrix materials mentioned in the applications which were yet to be published at the priority date of the present application and have the following reference numbers: PCT/EP2007/059648, EP 07 111 824.4.

In the case that at least one emitter material is used in the light-emitting layer of the inventive OLED together with at least one matrix material, the proportion of the at least one matrix material in the light-emitting layer of the inventive OLED is generally from 10 to 99% by weight, preferably from 50 to 99% by weight, more preferably from 70 to 97% by weight. The proportion of the at least one emitter material in the light-emitting layer is generally from 1 to 90% by weight, preferably from 1 to 50% by weight, more preferably from 3 to 30% by weight, where the proportions of the at least one matrix material and the at least one emitter material add up to 100% by weight. However, it is also possible that the light-emitting layer, as well as the at least one matrix material and the at least one emitter material, comprises further substances, for example further diluent material, further diluent material having been specified above.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:
  a hole injection layer between the anode (1) and the hole-transporting layer (2);
  a blocking layer for electrons and/or excitons between the hole-transporting layer (2) and the light-emitting layer (3);
  a blocking layer for holes and/or excitons between the light-emitting layer (3) and the electron-transporting layer (4);
  an electron injection layer between the electron-transporting layer (4) and the cathode (5).

As already mentioned above, it is, however, also possible that the OLED does not have all of the layers (1) to (5) mentioned; for example, an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

Those skilled in the art know how suitable materials have to be selected (for example on the basis of electrochemical investigations). Suitable materials for the individual layers and suitable OLED structures are known to those skilled in the art and disclosed, for example, in WO 2005/113704.

Furthermore, each of the specified layers of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed. Compositions which, in addition to the at least one inventive cyclometalated bridged carbene complex of the formula I, have a polymeric material in one of the layers of the OLED, preferably in the light-emitting layer, are generally applied as a layer by means of solution-processing processes.

In general, the different layers have the following thicknesses: anode (2) from 500 to 5000 Å, preferably from 1000 to 2000 Å; hole-transporting layer (3) from 50 to 1000 Å, preferably from 200 to 800 Å; light-emitting layer (4) from 10 to 1000 Å, preferably from 100 to 800 Å; electron-transporting layer (5) from 50 to 1000 Å, preferably from 200 to 800 Å; cathode (7) from 200 to 10 000 Å, preferably from 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the inventive cyclometalated bridged carbene complexes of the formula I in at least one layer of the inventive OLED, preferably as an emitter molecule in the light-emitting layer of the inventive OLEDs, allows OLEDs with high efficiency and long lifetime to be obtained. The efficiency of the inventive OLEDs may additionally be improved by optimizing the other layers. For example, highly efficient cathodes such as Ca, Ba or LiF may be used. Shaped substrates and novel hole-transporting materials which bring about a reduction in the operating voltage or an increase in the external quantum efficiency are likewise usable in the inventive OLEDs. Furthermore, additional layers may be present in the OLEDs in order to adjust the energy level of the different layers and to ease electroluminescence.

The inventive OLEDs may be used in all devices in which electroluminescence is useful. Suitable devices are preferably selected from stationary and mobile visual display units, and also illuminating means. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, vehicles and destination displays on buses and trains. Illuminating means are, for example, background lighting of LCDs, luminous surfaces, for example luminous wallpaper.

The inventive cyclometalated carbene complexes of the formula I, especially the preferred and particularly preferred embodiments of the inventive cyclometalated carbene complexes of the formula I specified in the present application, may, in a preferred embodiment, be used in an OLED as described in application PCT/EP2008/058106, which was yet to be published at the priority date of the present application, in which case the inventive cyclometalated carbene complex of the formula I preferably replaces the carbene complex of the general formula I present in the light-emitting layer specified in PCT/EP2008/058106. The inventive cyclometalated carbene complexes can be used as phosphorescent emitter substances in the OLED according to PCT/EP2008/058106. However, it is additionally possible that the inventive cyclometalated carbene complexes of the formula I, depending on the central metal used and the ligands used, and also on the further materials used in the OLEDs, are used as electron blockers, exciton blockers or hole blockers, or hole conductors, electron conductors, hole injection layers or matrix material (especially as matrix material in the light-emitting layer).

In addition, the inventive cyclometalated bridged carbene complexes of the formula I may be used in OLEDs with inverse structure. The inventive cyclometalated bridged carbene complexes of the formula I are preferably used in these inverse OLEDs again in the light-emitting layer. The structure of inverse OLEDs and the materials customarily used therein are known to those skilled in the art.

The above-described inventive cyclometalated bridged carbene complexes of the formula I may, in addition to the use in OLEDs, be used as colorants which emit in the visible region of the electromagnetic spectrum on irradiation by light (photoluminescence).

The present application therefore further provides for the use of the above-described inventive cyclometalated bridged carbene complexes of the formula I for the bulk coloration of polymeric materials.

Suitable polymeric materials are polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene, polyisoprene and the copolymers of the monomers listed.

In addition, the above-described inventive cyclometalated bridged carbene complexes of the formula I may be used in the following applications:

Use of the inventive cyclometalated bridged carbene complexes of the formula I as or in vat dye(s), for example for coloring natural materials; examples are paper, wood, straw, leather, pelts or natural fiber materials such as cotton, wool, silk, jute, sisal, hemp, flax or animal hairs (for example horsehair) and their conversion products, for example viscose fibers, nitrate silk or copper rayon.

Use of the inventive cyclometalated bridged carbene complexes of the formula I as colorants, for example for coloring paints, varnishes and other surface coating compositions, paper inks, printing inks, other inks and other colors for drawing and writing purposes.

Use of the inventive cyclometalated bridged carbene complexes of the formula I as pigmentary dyes, for example for coloring paints, varnishes and other surface coating compositions, paper inks, printing inks, other inks and other colors for drawing and writing purposes.

Use of the inventive cyclometalated bridged carbene complexes of the formula I as pigments in electrophotography: for example for dry copying systems (Xerox process) and laser printers.

Use of the inventive cyclometalated bridged carbene complexes of the formula I for security marking purposes, for which high chemical and photochemical stability and, if appropriate, also the luminescence of the substances is of significance. This is preferably for checks, check cards, banknotes, coupons, documents, identification papers and the like, in which a particular, unmistakable color impression is to be achieved.

Use of the inventive cyclometalated bridged carbene complexes of the formula I as an additive to other colors in which a particular shade is to be achieved; preference is given to particularly brilliant colors.

Use of the inventive cyclometalated bridged carbene complexes of the formula I for marking articles for machine recognition of these articles using the luminescence, preferably machine recognition of articles for sorting, including, for example, for the recycling of plastics.

Use of the inventive cyclometalated bridged carbene complexes of the formula I as luminescent dyes for machine-readable markings; preference is given to alphanumeric markings or barcodes.

Use of the inventive cyclometalated bridged carbene complexes of the formula I for adjusting the frequency of light, for example to convert short-wavelength light into longer-wavelength, visible light.

Use of the inventive cyclometalated bridged carbene complexes of the formula I in display elements for many kinds of display, information and marking purposes, for example in passive display elements, information signs and traffic signs, such as traffic lights.

Use of the inventive cyclometalated bridged carbene complexes of the formula I in inkjet printers, preferably in homogeneous solution as luminescent ink.

Use of the inventive cyclometalated bridged carbene complexes of the formula I as a starting material for superconductive organic materials.

Use of the inventive cyclometalated bridged carbene complexes of the formula I for solid-state luminescent markings.

Use of the inventive cyclometalated bridged carbene complexes of the formula I for decorative purposes.

Use of the inventive cyclometalated bridged carbene complexes of the formula I for tracer purposes, for example in biochemistry, medicine, engineering and natural sciences. In this use, the dyes can be bonded covalently to substrates or via secondary valences such as hydrogen bonds or hydrophobic interactions (adsorption).

Use of the inventive cyclometalated bridged carbene complexes of the formula I as luminescent dyes in high-sensitivity detection methods (cf. C. Aubert, J. Fünfschilling, I. Zschocke-Gränacher and H. Langhals, Z. Analyt. Chem. 320 (1985) 361).

Use of the inventive cyclometalated bridged carbene complexes of the formula I as luminescent dyes in scintillation devices.

Use of the inventive cyclometalated bridged carbene complexes of the formula I as dyes or luminescent dyes in optical light-collection systems.

Use of the inventive cyclometalated bridged carbene complexes of the formula I as dyes or luminescent dyes in luminescent solar collectors (cf. Langhals, Nachr. Chem. Tech. Lab. 28 (1980) 716).

Use of the inventive cyclometalated bridged carbene complexes of the formula I as dyes or luminescent dyes in luminescence-activated displays (cf. W. Greubel and G. Baur, Elektronik 26 (1977) 6).

Use of the inventive cyclometalated bridged carbene complexes of the formula I as dyes or luminescent dyes in cold light sources for light-induced polymerization for the production of plastics.

Use of the inventive cyclometalated bridged carbene complexes of the formula I as dyes or luminescent dyes for materials testing, for example in the production of semiconductor circuits.

Use of the inventive cyclometalated bridged carbene complexes of the formula I as dyes or luminescent dyes for the investigation of microstructures of integrated semiconductor components.

Use of the inventive cyclometalated bridged carbene complexes of the formula I as dyes or luminescent dyes in photoconductors.

Use of the inventive cyclometalated bridged carbene complexes of the formula I as dyes or luminescent dyes in photographic processes.

Use of the inventive cyclometalated bridged carbene complexes of the formula I as dyes or luminescent dyes in display, illumination or image conversion systems, in which excitation occurs by means of electrons, ions or UV radiation, for example in luminescent displays, Braun tubes or in fluorescent tubes.

Use of the inventive cyclometalated bridged carbene complexes of the formula I as dyes or luminescent dyes as part of an integrated semiconductor circuit, the dyes being used as such or in conjunction with other semiconductors, for example in the form of epitaxy.

Use of the inventive cyclometalated bridged carbene complexes of the formula I as dyes or luminescent dyes in chemiluminescent systems, for example in chemiluminescent illumination rods, in luminescent immunoassays or other luminescent detection methods.

Use of the inventive cyclometalated bridged carbene complexes of the formula I as dyes or luminescent dyes as signal colors, preferably for the optical emphasis of inscriptions and drawings or other graphical products, for individualizing signs and other articles in which a particular optical color impression is to be achieved.

Use of the inventive cyclometalated bridged carbene complexes of the formula I as dyes or luminescent dyes in dye lasers, preferably as luminescent dyes for generating laser beams.

Use of the inventive cyclometalated bridged carbene complexes of the formula I as active substances for nonlinear optics, for example for frequency doubling and frequency tripling of laser light.

Use of the inventive cyclometalated bridged carbene complexes of the formula I as rheology improvers.

Use of the inventive cyclometalated bridged carbene complexes of the formula I as dyes in photovoltaic arrays for the conversion of electromagnetic radiation to electrical energy.

The examples which follow provide additional illustration of the invention.

EXAMPLES

I) Synthesis Methods

Complexes with Triazolophenanthridine Ligands

Synthesis of 2-methyl

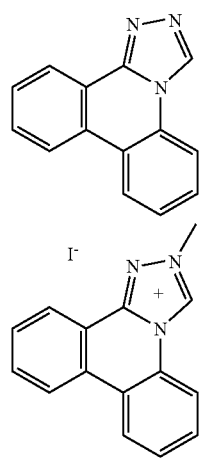

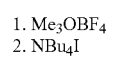

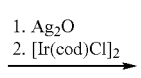

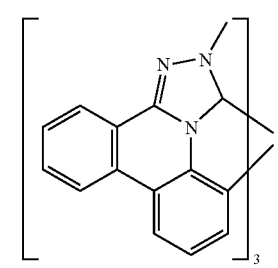

2-methyl

1-Methyl-1,2,4-triazolo[4,3-f]phenanthridinium tetrafluoroborate

A solution of 1,2,4-triazolo[4,3-f]phenanthridine (A. G. Mikhailovskii, V. S. Shklyaev, *Chem. Heterocycl. Comp.* 1992, 445) (5.9 g, 27 mmol) in dichloromethane (200 ml) and methanol (20 ml) is admixed under argon at 2° C. with trimethyloxonium tetrafluoroborate (4.3 g, 29 mmol) and stirred at 2° C. for 1 h and at room temperature for 16 h. The resulting precipitate is filtered off and washed with dichloromethane, methanol and petroleum ether. Yield: 5.9 g (69%).

$^1$H NMR (d$_6$-DMSO, 400 MHz): δ=4.39 (s, 3H), 7.84-7.98 (m, 3H), 8.04 (td, 1H), 8.41 (dd, 1H), 8.54 (dd, 1H), 8.83 (dd, 1H), 8.86 (dd, 1H), 11.47 (s, 1H).

1-Methyl-1,2,4-triazolo[4,3-f]phenanthridinium iodide

A suspension of 1-methyl-1,2,4-triazolo[4,3-f]phenanthridinium tetrafluoroborate (4.7 g, 5.9 mmol) in methanol (80 ml) is admixed under argon with tetrabutylammonium iodide (6.5 g, 17.6 mmol) and stirred under reflux for 11 h. After cooling to room temperature, the precipitate is filtered off and washed with methanol. Yield: 4.1 g of a mixture of iodide and tetrafluoroborate salt (3:1, 83%).

Elemental analysis: calc. for C$_{14}$H$_{13}$IN$_3$/C$_{14}$H$_{13}$BF$_4$N$_3$ (3:1): C, 51.44; H, 3.46; N, 12.00, 126.36. found: C, 51.4; H, 3.5; N, 12.0, 126.3.

mer-tris[1-Methyl-1,2,4-triazolo[4,3-f]phenanthridin-5-ylidene-C5,C6]iridium(III)

A suspension of 1-methyl-1,2,4-triazolo[4,3-f]phenanthridinium iodide (4.0 g, 11.0 mmol) and silver(I) oxide (1.3 g, 5.5 mmol) in methanol (200 ml) is stirred under argon at room temperature for 16 h. The mixture is diluted with methanol (70 ml) and stirred for a further 5 h. The precipitate is filtered off and washed with methanol and petroleum ether. Yield: 4.9 g (94%). A mixture of the silver carbene (4.8 g, 5.1 mmol) and of 1,5-cyclooctadieneiridium(I) chloride dimer (0.7 g, 1.1 mmol) in mesitylene (200 ml) is stirred under reflux under argon for 20 h. After cooling to room temperature, the precipitate is filtered off and washed with toluene. The combined filtrates are concentrated to dryness and purified by column chromatography (alumina, 4:1 dichloromethane/toluene). Yield: 1.4 g (75%).

$^1$H NMR (d$_6$-DMSO, 400 MHz): δ=3.47 (s, 3H), 3.60 (s, 3H), 3.68 (s, 3H), 6.81 (d, 1H), 6.93 (d, 1H), 7.00-7.09 (m, 5H), 7.18 (d, 1H), 7.25 (d, 1H), 7.68-7.76 (m, 3H), 7.81-7.96 (m, 6H), 8.30-8.38 (m, 3H), 8.56-8.64 (m, 3H).

Synthesis of 2-o-tolyl

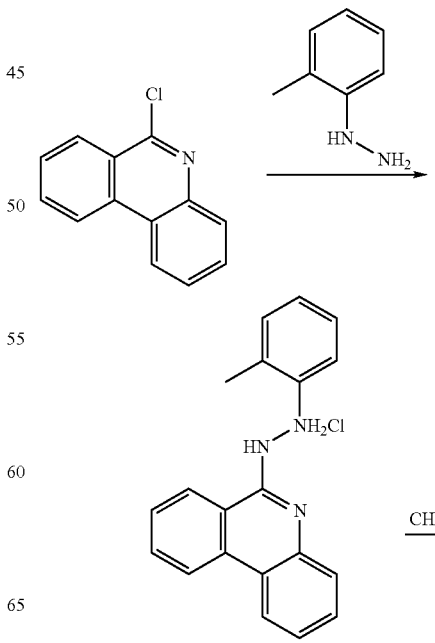

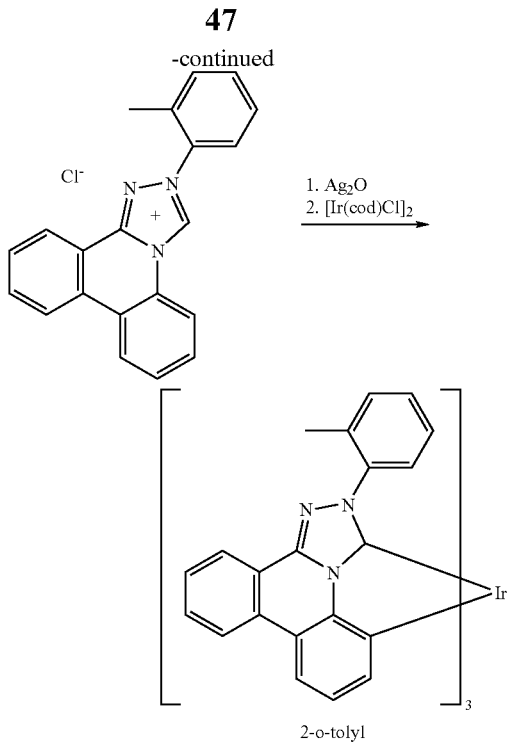

2-o-tolyl

N-Phenanthridin-6-yl-N'-o-tolylhydrazine hydrochloride

A solution of o-tolylhydrazine hydrochloride (7.6 g, 47 mmol) in dichloromethane (450 ml) is extracted by shaking three times each with saturated aqueous sodium hydrogencarbonate solution (90 ml each time) and demineralized water. The organic phase is dried over sodium sulfate, filtered and concentrated to dryness. Yield: 4.9 g (86%). The hydrazine (4.8 g, 39 mmol) is dissolved in ethanol (100 ml) and admixed under argon with 6-chlorophenanthridine (A. G. Mikhailovskii, V. S. Shklyaev, Chem. Heterocycl. Comp. 1992, 445) (7.0 g, 33 mmol). The mixture is stirred under reflux for 16 h. After cooling to room temperature, the resulting precipitate is filtered off and washed with ethanol and petroleum ether. Yield: 9.3 g (85%).

$^1$H NMR ($d_6$-DMSO, 400 MHz): δ=2.41 (s, 3H), 6.90 (t, 1H), 6.97 (d, 1H), 7.11 (t, 1H), 7.20 (d, 1H), 7.60 (t, 1H), 7.74 (t, 1H), 7.92 (t, 1H), 8.16 (t, 1H), 8.24 (d, 1H), 8.30 (br s, 1H), 8.71 (d, 1H), 8.88 (d, 1H), 8.89 (d, 1H), 12.23 (br s, 1H), 13.02 (br s, 1H).

1-o-Tolyl-1,2,4-triazolo[4,3-f]phenanthridinium chloride

A suspension of N-phenanthridin-6-yl-N'-o-tolylhydrazine hydrochloride (9.0 g, 27 mmol) in triethyl orthoformate (360 ml) is stirred under reflux under argon for 17 h. After cooling to room temperature, the precipitate is filtered off and washed with triethyl orthoformate and cold acetone. Yield: 8.2 g (88%).

$^1$H NMR ($d_6$-DMSO, 400 MHz): δ=2.47 (s, 3H), 7.56-7.73 (m, 3H), 7.81 (d, 1H), 7.90-8.02 (m, 3H), 8.09 (t, 1H), 8.63 (d, 1H), 8.70 (d, 1H), 8.90 (d, 1H), 8.93 (d, 1H), 12.22 (s, 1H).

mer-tris[1-o-Tolyl-1,2,4-triazolo[4,3-f]phenanthridin-5-ylidene-C5,C6]iridium(III)

A suspension of 1-o-tolyl-1,2,4-triazolo[4,3-f]phenanthridinium chloride (10.0 g, 28.8 mmol) and silver(I) oxide (3.3 g, 14.4 mmol) in methanol (1200 ml) is stirred under argon at room temperature for 44 h. The precipitate is filtered off and washed with methanol and petroleum ether. Yield: 10.5 g (80%). A mixture of the silver carbene (10.5 g, 11.6 mmol) and of 1,5-cyclooctadieneiridium(I) chloride dimer (1.6 g, 2.3 mmol) in mesitylene (420 ml) is stirred under reflux under argon for 16 h. After cooling to room temperature, the precipitate is filtered off and washed with dichloromethane. The combined filtrates are concentrated to dryness and the residue is purified by column chromatography (alumina, 1:1 dichloromethane/cyclohexane). Yield: 1.6 g (25%) of fac-isomer and 1.5 g (25%) of mer-isomer.

fac-Isomer: $^1$H NMR (CD$_2$Cl$_2$, 400 MHz): δ=1.51 (s, 9H), 6.47 (br s, 3H), 6.65 (m$_c$, 6H), 6.73 (d, 3H), 6.94 (dd, 3H), 7.01 (dd, 3H), 7.59 (dd, 3H), 7.76 (d, 3H), 7.80 (dd, 3H), 8.23 (d, 3H), 8.45 (d, 3H). mer-Isomer: $^1$H NMR (CD$_2$Cl$_2$, 400 MHz): δ=1.02 (s, 3H), 1.51 (s, 3H), 1.71 (s, 3H), 5.85 (br s, 1H), 6.22 (br s, 1H), 6.29 (d, 1H), 6.44 (br s, 1H), 6.52-6.74 (m, 7H), 6.80 (dd, 1H), 6.82 (dd, 1H), 7.00-7.14 (m, 3H), 7.31 (br s, 1H), 7.40 (d, 1H), 7.49 (d, 1H), 7.56 (dd, 1H), 7.58 (dd, 1H), 7.64 (dd, 1H), 7.69-7.84 (m, 5H), 8.28-8.43 (m, 6H).

Synthesis of 2-phenyl

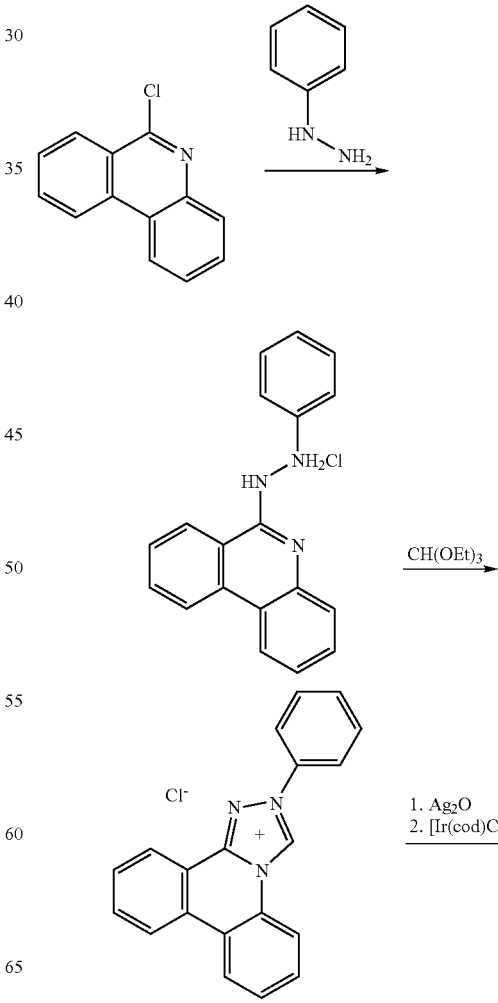

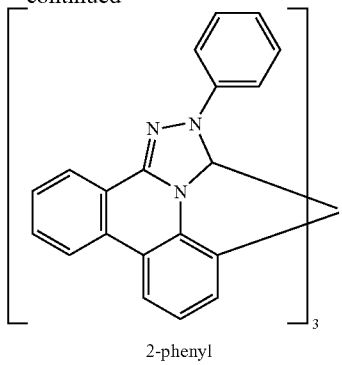

2-phenyl

N-Phenanthridin-6-yl-N'-phenylhydrazine hydrochloride

Phenylhydrazine (1.3 g, 12 mmol) is dissolved in ethanol (50 ml) and admixed under argon with 6-chlorophenanthridine (A. G. Mikhailovskii, V. S. Shklyaev, Chem. Heterocycl. Comp. 1992, 445) (2.1 g, 10 mmol). The mixture is stirred under reflux for 16 h. After cooling to room temperature, the mixture is concentrated and the resulting precipitate is filtered off and washed with methyl tert-butyl ether. Yield: 2.6 g (82%).

$^1$H NMR (d$_6$-DMSO, 400 MHz): δ=6.95 (t, 1H), 7.10 (d, 2H), 7.29 (t, 2H), 7.55 (br s, 1H), 7.69 (br t, 1H), 7.88 (br t, 1H), 8.11 (br s, 1H), 8.17 (br s, 1H), 8.65 (br s, 1H), 8.84 (br s, 2H), 8.99 (br s, 1H), 12.30 (br s, 1H), 13.05 (br s, 1H).

1-Phenyl-1,2,4-triazolo[4,3-f]phenanthridinium chloride

A suspension of N-phenanthridin-6-yl-N'-phenylhydrazine hydrochloride (2.0 g, 6.2 mmol) in triethyl orthoformate (100 ml) is stirred under reflux under argon for 17 h. After cooling to room temperature, the mixture is concentrated and the precipitate is filtered off and washed with petroleum ether, methyl tert-butyl ether and acetone. Yield: 1.2 g (57%).

$^1$H NMR (d$_6$-DMSO, 400 MHz): δ=7.74 (t, 1H), 7.82 (t, 2H), 7.88-8.01 (m, 3H), 8.08 (t, 1H), 8.31 (d, 2H), 8.68 (d, 1H), 8.80 (d, 1H), 8.86 (d, 1H), 8.88 (d, 1H), 12.62 (s, 1H).

mer-tris[1-Phenyl-1,2,4-triazolo[4,3-f]phenanthridin-5-ylidene-C5,C6]iridium(III)

A suspension of 1-phenyl-1,2,4-triazolo[4,3-f]phenanthridinium chloride (1.18 g, 3.6 mmol) and silver(I) oxide (0.42 g, 1.8 mmol) in methanol (200 ml) is stirred under argon at room temperature for 32 h. The precipitate is filtered off and washed with methanol. Yield: 1.24 g (78%). A mixture of the silver carbene (1.24 g, 1.4 mmol) and of 1,5-cyclooctadieneiridium(I) chloride dimer (0.19 g, 0.3 mmol) in mesitylene (100 ml) is stirred under reflux under argon for 16 h. After cooling to room temperature, the precipitate is filtered off and washed with ethyl acetate. The combined filtrates are concentrated to dryness and the residue is purified by column chromatography (silica gel, 1:1 ethyl acetate/cyclohexane). Yield: 0.03 g (5%) of fac-isomer, 0.01 g (2%) of mer-isomer and 0.34 g (57%) of isomer mixture.

fac-Isomer: $^1$H NMR (CD$_2$Cl$_2$, 400 MHz): δ=6.16 (d, 6H), 6.88 (d, 3H), 6.93 (dd, 6H), 7.11 (dd, 3H), 7.26 (dd, 3H), 7.63 (dd, 3H), 7.80 (dd, 3H), 7.87 (d, 3H), 8.35 (d, 3H), 8.49 (d, 3H). ESI-MS: m/z=1074.2786 (calc. for M+H$^+$: 1074.2778).

mer-Isomer: $^1$H NMR (CD$_2$Cl$_2$, 400 MHz): S=6.29-6.37 (m, 2H), 6.44 (d, 1H), 6.47 (dd, 1H), 6.54 (dd, 2H), 6.66 (d, 1H), 6.78 (dd, 1H), 6.95 (dd, 2H), 7.00-7.23 (m, 9H), 7.55-7.79 (m, 8H), 7.84 (d, 1H), 8.15 (d, 1H), 8.29 (d, 1H), 8.34 (d, 1H), 8.39 (d, 1H), 8.43 (dd, 2H), 8.55 (d, 1H), 8.98 (d, 1H).

Synthesis of 2-isopropyl

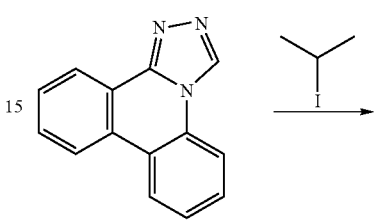

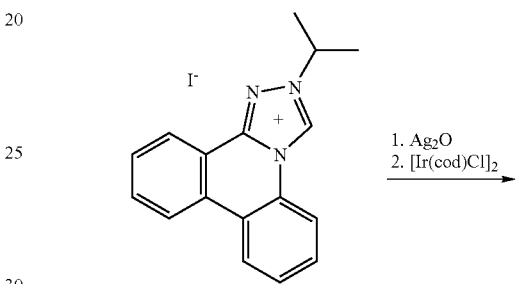

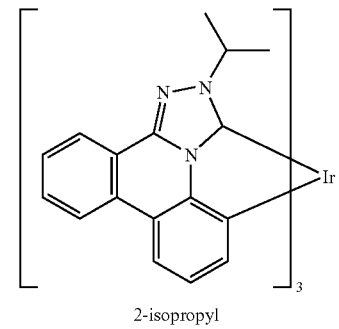

2-isopropyl

The complex 2-isopropyl is prepared analogously to the synthesis of 2-methyl proceeding from 1,2,4-triazolo[4,3-f]phenanthridine (A. G. Mikhailovskii, V. S. Shklyaev, Chem. Heterocycl. Comp. 1992, 445).

ESI-MS: m/z=973 (calc. for M+H$^+$: 973).

Synthesis of 2-p-pyridyl

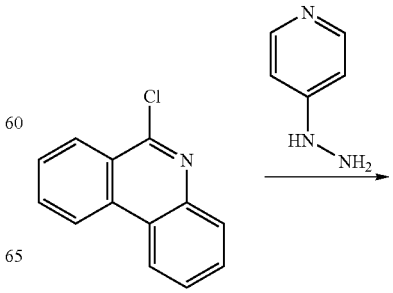

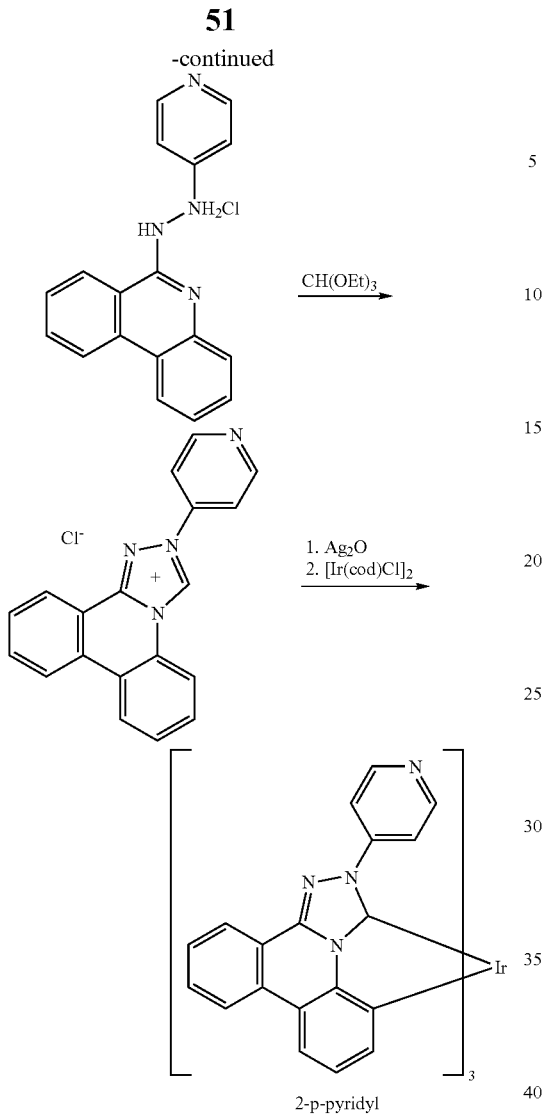

2-p-pyridyl

The complex 2-p-pyridyl is prepared analogously to the synthesis of 2-phenyl proceeding from chlorophenanthridine (A. G. Mikhailovskii, V. S. Shklyaev, *Chem. Heterocycl. Comp.* 1992, 445) and 4-hydrazinopyridine (E. M. Isin, M. Jonge, N. Castagnoli, *J. Org. Chem.* 2001, 66, 4220).

2-p-Pyridyl: ESI-MS: m/z=1078 (calc. for M+H$^+$: 1078).

II) Photophysical Characterization

The photoluminescence of the emitting complexes was carried out in thin PMMA films (polymethyl methacrylate) with an emitter doping of 2%. The films were produced as follows: 2 mg/l of emitter were dissolved in a 10% PMMA solution in DCM (Mw 120 kD) and applied to a microscope slide with a 60 μm doctor blade. The excitation was effected at a wavelength of 325 nm (HeCd laser) at right angles to the microscope slide, and the emission was detected at an angle of 45° by means of fiber optics in a diode array spectrometer.

| Complex | $\lambda_{max}$ [nm] | QA [%] | CIE x | CIE y |
|---|---|---|---|---|
| 2-Methyl (mer-isomer) | 448, 481 | 45 | 0.15 | 0.18 |
| 2-Phenyl (fac-isomer) | 448, 475 | 45 | 0.15 | 0.17 |
| 2-Phenyl (mer-isomer) | 452, 478 | 65 | 0.15 | 0.18 |
| 2-o-Tolyl (fac-isomer) | 445, 473 | 71 | 0.15 | 0.15 |
| 2-o-Tolyl (mer-isomer) | 449, 475 | 49 | 0.15 | 0.18 |

III) OLED Device Tests

III.1) Light-Emitting Layer: Compound of the Formula I+Silylcarbazole

The ITO substrate used as the anode is first cleaned with commercial detergents for LCD production (Deconex® 20NS and 250RGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection of the ITO.

Thereafter, the organic materials mentioned below are applied by vapor deposition to the cleaned substrate at a rate of 0.5-5.0 nm/min at about 10$^{-8}$ mbar. As a hole conductor and exciton blocker, the compound V1 is first applied to the substrate in a layer thickness of 45 nm.

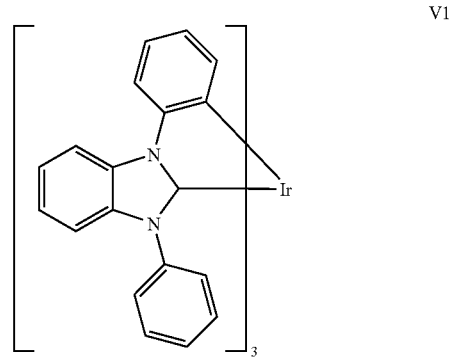

V1

(for the preparation of compound V1, see Ir complex (7) in WO 2005/019373.)

Subsequently, a mixture of 6.5% by weight of the compound 2-methyl

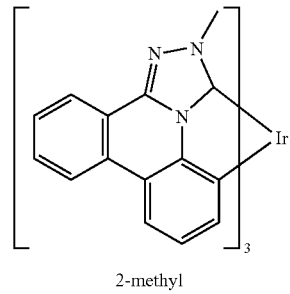

2-methyl and 93.5% by weight of the compound V2

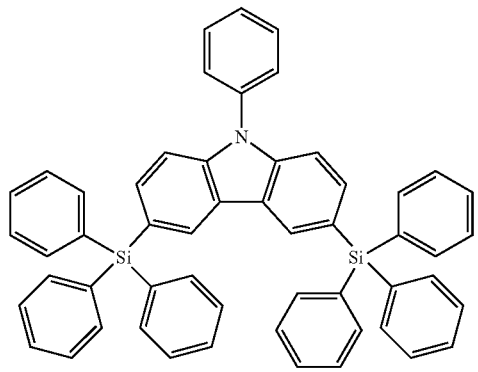

V2

(for the preparation of compound V2, see example (4b) in the application EP 07 111 824.4, which was yet to be published at the priority date of the present application (title: "Organic light-emitting diodes comprising at least one disilyl compound selected from disilylcarbazoles, disilyldibenzofurans, disilyldibenzothiophenes, disilyldibenzophospholes, disilyldibenzo-thiophene S-oxides and disilyldibenzothiophene S,S-dioxides").

is applied by vapor deposition in a thickness of 40 nm, 2-methyl functioning as an emitter and V2 as a matrix material. Thereafter, an exciton blocker layer composed of V2 is applied by vapor deposition in a thickness of 10 nm.

Thereafter, an electron conductor layer composed of BCP (2,9-dimethyl-4,7-diphenyl-1,10-phenanthroline) is applied by vapor deposition in a thickness of 45 nm, as are a 0.7 nm-thick lithium fluoride layer and finally a 100 nm-thick Al electrode.

To characterize the OLEDs, electroluminescence spectra are recorded at various currents and voltages. In addition, the current-voltage characteristic is measured in combination with the emitted light output. The light output can be converted to photometric parameters by calibration with a photometer. To determine the lifetime, the OLED is operated at a constant current density and the decrease in the light output is recorded. The lifetime is defined as that time which elapses until the luminance has decreased to half of the initial luminance.

For the OLED described, the following electrooptical data are obtained:

| | |
|---|---|
| Emission maximum | 452, 479 nm |
| CIE(x, y) | 0.15; 0.18 |
| Photometric efficiency | 13.4 cd/A (max.) |
| External quantum yield | 7.2% (max.) |
| Maximum luminance | 1300 cd/m² (max.) |

III.2) Light-Emitting Layer: Compound of the Formula I+Ir(dpbic)$_3$

The ITO substrate used as the anode is first cleaned with commercial detergents for LCD production (Deconex® 20NS and 250RGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO.

Thereafter, the organic materials specified below are applied by vapor deposition to the cleaned substrate at a rate of approx. 0.5-5 nm/min at about $10^{-8}$ mbar. The hole conductor and exciton blocker applied to the substrate is Ir(dpbic)$_3$ with a thickness of 45 nm.

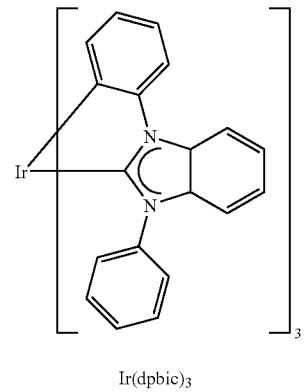

Ir(dpbic)$_3$ (for preparation see Ir complex (7) in application WO 2005/019373).

Subsequently, a mixture of 7% by weight of the compound 2-R

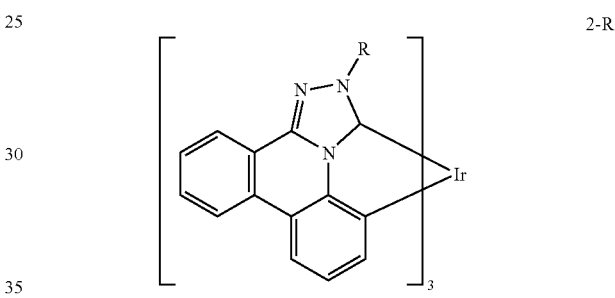

2-R and 93% by weight of the compound Ir(dpbic)$_3$ is applied by vapor deposition in a thickness of 40 nm, the former compound functioning as the emitter, the latter as the matrix material.

Subsequently, the material 9-(4-phenyl)-3,6-bis(triphenylsilyl)-9H-carbazole is applied by vapor deposition with a thickness of 10 nm as an exciton and hole blocker.

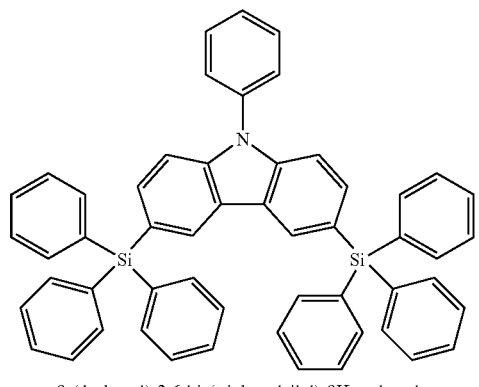

9-(4-phenyl)-3,6-bis(triphenylsilyl)-9H-carbazole

Next, an electron transporter BCP (2,9-dimethyl-4,7-diphenyl-1,10-phenanthroline) is applied by vapor deposition in a thickness of 45 nm, as are a 0.75 nm-thick lithium fluoride layer and finally a 110 nm-thick Al electrode.

To characterize the OLEDs, electroluminescence spectra are recorded at different currents and voltages. In addition, the current-voltage characteristic is measured in combination with the light output emitted. The light output can be converted to photometric parameters by calibration with a photometer.

For the OLEDs described, the following electrooptical data are obtained:

| R = | Material | Emission maximum (nm) | CIE (x, y) | Photometric efficiency at 4 V (cd/A) | Power efficiency at 4 V (lm/W) | External quantum yield at 4 V (%) | Luminance at 10 V (cd/m$^2$) |
|---|---|---|---|---|---|---|---|
| methyl | 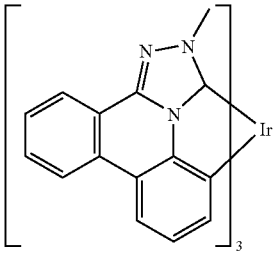 2-Methyl<br>2-Methyl mer isomer | 451/478 | 0.16; 0.21 | 13.2 | 10.4 | 7.1 | 490 |
| o-tolyl | 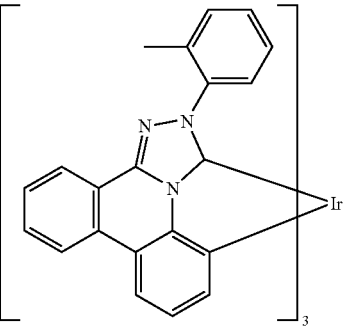 2-o-Tolyl<br>2-o-tolyl mer isomer | 455/478 | 0.17; 0.2 | 7.7 | 6.0 | 5.1 | 810 |
| o-tolyl | 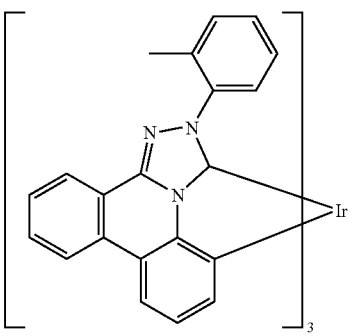 2-o-Tolyl<br>2-o-tolyl fac isomer | 448/476 | 0.16; 0.16 | 9.1 | 7.2 | 6.7 | 740 |

| R = | Material | Emission maximum (nm) | CIE (x, y) | Photometric efficiency at 4 V (cd/A) | Power efficiency at 4 V (lm/W) | External quantum yield at 4 V (%) | Luminance at 10 V (cd/m$^2$) |
|---|---|---|---|---|---|---|---|
| i-propyl | 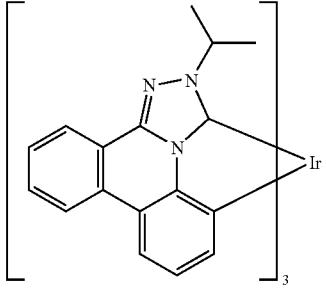<br>2-Isopropyl<br>2-isopropyl mer isomer | 449/476 | 0.16; 0.19 | 14.6 | 11.4 | 9.9 | 575 |
| phenyl | 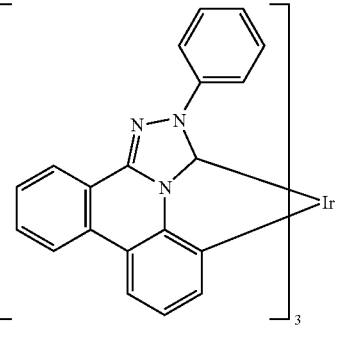<br>2-Phenyl<br>2-phenyl fac isomer | 449/476 nm | 0.16; 0.17 | 15 | 11.8 | 11.2 | 890 |

The invention claimed is:

1. A cyclometalated carbene complex of the general formula (I)

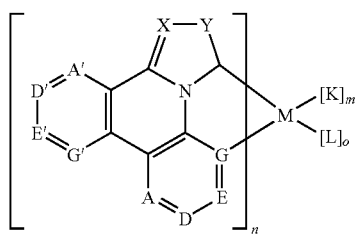

in which the symbols are each defined as follows:

M is a metal atom selected from the group consisting of metals of group IB, IIB, IIIB, IVB, VB, VIIB, VIIB, VIIIB, the lanthanides and IIIA of the Periodic Table of the Elements (CAS version) in any oxidation state possible for the appropriate metal atom;

K is an uncharged mono- or bidentate ligand;

L is a mono- or dianionic ligand;

X is $CR^1$ or N;

Y is $NR^2$ or $CR^2{}_2$;

A, D, G, E, A', D', G' and E'
are each independently CH, $CR^3$ or N;

$R^1$ is F, CN, $C_1$-$C_{20}$-alkoxy, $C_6$-$C_{30}$-aryloxy, $C_1$-$C_{20}$-alkylthio, $C_6$-$C_{30}$-arylthio, substituted or unsubstituted $C_6$-$C_{30}$-aryl or substituted or unsubstituted heteroaryl having from 5 to 30 ring atoms;

$R^2$, $R^3$
are each independently substituted or unsubstituted $C_1$-$C_{20}$-alkyl, substituted or unsubstituted $C_5$-$C_{20}$-cycloalkyl, substituted or unsubstituted $C_5$-$C_{20}$-cycloalkenyl, substituted or unsubstituted heterocycloalkyl having from 5 to 30 ring atoms, substituted or unsubstituted heterocycloalkenyl having from 5 to 30 ring atoms, substituted or unsubstituted $C_2$-$C_{20}$-alkenyl, substituted or unsubstituted $C_2$-$C_{20}$-alkynyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals, carbonyl (—CO($R^4$)), carbonylthio (—C=O($SR^4$)), carbonyloxy (—C=O($OR^4$)), oxycarbonyl (—OC=O($R^4$)), thiocarbonyl (—SC=O($R^4$)), amino (—$NR^4R^5$), OH, pseudohalogen radicals, amido (—C=O($NR^4R^5$)), —$NR^4$C=O($R^5$), phosphonate (—P(O)($OR^4$)$_2$), phosphate (—OP(O)($OR^4$)$_2$), phosphine (—$PR^4R^5$), phosphine oxide (—P(O)$R^4{}_2$), sulfate (—OS(O)$_2OR^4$), sulfoxide (—S(O)$R^4$), sulfonate (—S(O)$_2OR^4$), sulfonyl (—S(O)$_2R^4$), sulfonamide (—S(O)$_2NR^4R^5$), NO$_2$, boronic esters (—B($OR^4$)$_2$), imino (—C=$NR^4R^5$), borane radicals, stannate radicals, hydrazine radicals, hydrazone radicals, oxime radicals, nitroso groups, diazo groups, vinyl groups, sulfoximines, alanes, germanes, boroxines and borazines;
or
two adjacent $R^3$ radicals together form a saturated or unsaturated, substituted or unsubstituted bridge comprising from 3 to 6 atoms, wherein the $R^3$ radicals together with one of the elements A=D, D-E, D'-E', E'=G' form a 5- to 8-membered ring;

or the $R^3$ radicals at the G' and A positions together form a saturated or unsaturated, substituted or unsubstituted bridge comprising from 1 to 4 atoms, wherein the $R^3$ radicals together with the element -G'-C—C-A- form a 5- to 8-membered ring;

$R^4$, $R^5$, $R^6$ are each independently H, substituted or unsubstituted $C_1$-$C_{20}$-alkyl or substituted or unsubstituted $C_6$-$C_{30}$-aryl or substituted or unsubstituted heteroaryl having from 5 to 30 ring atoms;

n is a number of carbene ligands, where n is at least 1 and the carbene ligands in the complex of the formula I, when n>1, are the same or different;

m is a number of ligands K, where m is 0 or $\geq 1$, and the ligands K, when m>1, are the same or different;

o is a number of ligands L, where o is 0 or $\geq 1$, and the ligands L, when o>1, are the same or different;

where the sum of n+m+o depends on the oxidation state and coordination number of the metal atom used and on the denticity of the ligands L and K, and also on the charge of the ligand L, with the condition that n is at least 1.

2. The carbene complex according to claim 1, wherein M is Ir(III), n is 3, and m, o are each 0.

3. The carbene complex according to claim 1, wherein $R^2$, $R^3$ are each independently selected from the group consisting of substituted or unsubstituted $C_1$-$C_{20}$-alkyl, substituted or unsubstituted $C_2$-$C_{20}$-alkenyl, substituted or unsubstituted $C_2$-$C_{20}$-alkynyl, substituted or unsubstituted $C_6$-$C_{30}$-aryl, substituted or unsubstituted heteroaryl having from 5 to 30 ring atoms, $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals and pseudohalogen radicals;

or two adjacent $R^3$ radicals together form a saturated or unsaturated, methyl-, methoxy-, phenyl-, SiMe$_3$-, SiPh$_3$-, F-, CF$_3$- or CN-substituted or unsubstituted bridge comprising 3 or 4 carbon atoms, wherein the $R^3$ radicals together with one of the elements A=D, D-E, A'=D', D'-E', E'=G' form a 5- or 6-membered ring;

or the $R^3$ radicals at the G' and A positions together form a saturated or unsaturated, methyl-, methoxy-, phenyl-, SiMe$_3$-, SiPh$_3$-, F—, CF$_3$— or CN-substituted or unsubstituted bridge comprising 1 or 2 carbon atoms, wherein the $R^3$ radicals together with the element -G'-C—C-A- form a 5- or 6-membered ring.

4. The carbene complex according to claim 1, wherein $R^2$ is selected from the group consisting of substituted or unsubstituted $C_1$-$C_{20}$-alkyl which is branched in the 1-position, substituted or unsubstituted $C_6$-aryl, and substituted or unsubstituted heteroaryl having from 5 to 13 ring atoms.

5. The carbene complex according to claim 1, wherein X is N, and is $NR^2$.

6. The carbene complex according to claim 1, wherein A, D, G, E, A', D', G' and E' are each CH or $CR^3$.

7. The carbene complex according to claim 1, wherein the carbene complex is selected from the group consisting of

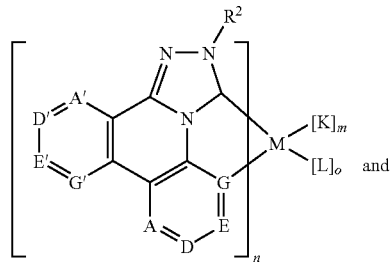

(Ia)

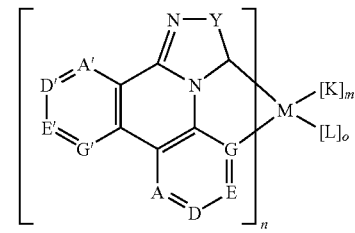

(Ib)

in which:

A, D, G, E, A', D', G' and E' are each independently CH, $CR^3$ or N, preferably CH or $CR^3$;

$R^2$, $R^3$ are each independently substituted or unsubstituted $C_1$-$C_{20}$-alkyl, substituted or unsubstituted $C_5$-$C_{20}$-cycloalkyl, substituted or unsubstituted $C_5$-$C_{20}$-cycloalkenyl, substituted or unsubstituted heterocycloalkyl having from 5 to 30 ring atoms, substituted or unsubstituted heterocycloalkenyl having from 5 to 30 ring atoms, substituted or unsubstituted $C_2$-$C_{20}$-alkenyl, substituted or unsubstituted $C_2$-$C_{20}$-alkynyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals, carbonyl (—CO($R^4$)), carbonylthio (—C=O($SR^4$)), carbonyloxy (—C=O($OR^4$)), oxycarbonyl (—OC=O($R^4$)), thiocarbonyl (—SC=O($R^4$)), amino (—$NR^4R^5$), OH, pseudohalogen radicals, amido (—C=O($NR^4R^5$)), —$NR^4$C=O($R^5$), phosphonate (—P(O)($OR^4$)$_2$), phosphate (—OP(O)($OR^4$)$_2$), phosphine (—$PR^4R^5$), phosphine oxide (—P(O)$R^4_2$), sulfate (—OS(O)$_2OR^4$), sulfoxide (—S(O)$R^4$), sulfonate (—S(O)$_2OR^4$), sulfonyl (—S(O)$_2R^4$), sulfonamide (—S(O)$_2NR^4R^5$), NO$_2$, boronic esters (—B(OR$^4$)$_2$), imino (—C=$NR^4R^5$), borane radicals, stannate radicals, hydrazine radicals, hydrazone radicals, oxime radicals, nitroso groups, diazo groups, vinyl groups, sulfoximines, alanes, germanes, boroxines and borazines;

or two adjacent $R^3$ radicals together form a saturated or unsaturated, substituted or unsubstituted bridge composed of from 3 to 6 atoms, wherein the $R^3$ radicals together with one of the elements A=D, D-E, A'=D', D'-E', E'=G' form a 5- to 8-membered ring;

or the $R^3$ radicals at the G' and A positions together form a saturated or unsaturated, substituted or unsubstituted bridge composed of from 1 to 4 atoms, wherein the $R^3$ radicals together with the element -G'-C—C-A- form a 5- to 8-membered ring;

$R^4$, $R^5$, $R^6$
are each independently H, substituted or unsubstituted $C_1$-$C_{20}$-alkyl or substituted or unsubstituted $C_6$-$C_{30}$-aryl, or substituted or unsubstituted heteroaryl having from 5 to 30 ring atoms;

Y is $CR^2_2$;

M is Ir, Os or Pt;

K is an uncharged bidentate ligand;

L is a monoanionic bidentate ligand;

n is the number of carbene ligands, where n is 3 in the case of Ir, is 2 in the case of Os and is 1 or 2 in the case of Pt, and the carbene ligands in the complexes of the formulae Ia, Ib, Ic and Id are the same or different;

m is 0 in the case that M=Ir or Pt and is 1 in the case of Os;

o is 0 in the case that M=Ir or Os and Pt and in the case that n=2, and is 1 in the case of Pt and in the case that n=1.

8. A process for preparing a carbene complex according to claim 1, comprising a reaction of at least one ligand precursor of the formula (III)

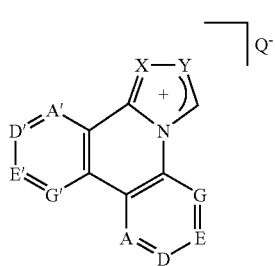

(III)

in which

Q is a monoanionic counterion;

X is $CR^1$ or N;

Y is $NR^2$ or $CR^2_2$;

A, D, G, E, A', D', G' or E'
are each independently CH, $CR^3$ or N;

$R^1$ is F, CN, $C_1$-$C_{20}$-alkoxy, $C_6$-$C_{30}$-aryloxy, $C_1$-$C_{20}$-alkylthio, $C_6$-$C_{30}$-arylthio, substituted or unsubstituted $C_6$-$C_{30}$-aryl or substituted or unsubstituted heteroaryl having from 5 to 30 ring atoms;

$R^2$, $R^3$
are each independently substituted or unsubstituted $C_1$-$C_{20}$-alkyl, substituted or unsubstituted $C_5$-$C_{20}$-cycloalkyl, substituted or unsubstituted $C_5$-$C_{20}$-cycloalkenyl, substituted or unsubstituted heterocycloalkyl having from 5 to 30 ring atoms, substituted or unsubstituted heterocycloalkenyl having from 5 to 30 ring atoms, substituted or unsubstituted $C_2$-$C_{20}$-alkenyl, substituted or unsubstituted $C_2$-$C_{20}$-alkynyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^4R^5R^6$, halogen radicals, halogenated $C_1$-$C_{20}$-alkyl radicals, carbonyl (—CO($R^4$)), carbonylthio (—C=O($SR^4$)), carbonyloxy (—C=O($OR^4$)), oxycarbonyl (—OC=O($R^4$)), thiocarbonyl (—SC=O($R^4$)), amino (—$NR^4R^5$), OH, pseudohalogen radicals, amido (—C=O($NR^4R^5$)), —$NR^4$C=O($R^5$), phosphonate (—P(O)($OR^4$)$_2$), phosphate (—OP(O)($OR^4$)$_2$), phosphine (—$PR^4R^5$), phosphine oxide (—P(O)$R^4_2$), sulfate (—OS(O)$_2OR^4$), sulfoxide (—S(O)$R^4$), sulfonate (—S(O)$_2OR^4$), sulfonyl (—S(O)$_2R^4$), sulfonamide (—S(O)$_2NR^4R^5$), $NO_2$, boronic esters (—B($OR^4$)$_2$), imino (—C=$NR^4R^5$), borane radicals, stannate radicals, hydrazine radicals, hydrazone radicals, oxime radicals, nitroso groups, diazo groups, vinyl groups, sulfoximines, alanes, germanes, boroxines and borazines;

or two adjacent $R^3$ radicals together form a saturated or unsaturated, substituted or unsubstituted bridge composed of from 3 to 6 atoms, wherein the $R^3$ radicals together with one of the elements A=D, D-E, A'=D', D'-E', E'=G' form a 5- to 8-membered ring;

or the $R^3$ radicals at the G' and A positions together form a saturated or unsaturated, substituted or unsubstituted bridge composed of from 1 to 4 atoms, wherein the $R^3$ radicals together with the element -G'-C—C-A- form a 5- to 8-membered ring;

and $R^4$, $R^5$, $R^6$
are each independently H, substituted or unsubstituted $C_1$-$C_{20}$-alkyl or substituted or unsubstituted $C_6$-$C_{30}$-aryl or substituted or unsubstituted heteroaryl having from 5 to 30 ring atoms;

with a metal complex comprising at least one metal M where

M is a metal atom selected from the group consisting of metals of group IB, IIB, IIIB, IVB, VB, VIIB, VIIB, VIIIB, the lanthanides and IIIA of the Periodic Table of the Elements (CAS version) in any oxidation state possible for the appropriate metal atom.

9. The process according to claim 8, wherein the metal M used is Ir, Os or Pt.

10. An organic light-emitting diode comprising at least one carbene complex according to claim 1.

11. A light-emitting layer comprising at least one carbene complex according to claim 1.

12. An organic light-emitting diode comprising at least one light-emitting layer according to claim 11.

13. A device selected from the group consisting of stationary visual display units, mobile visual display units, and illuminating means, comprising at least one organic light-emitting diode according to claim 12.

14. A device selected from the group consisting of stationary visual display units, mobile visual display units and illuminating means, comprising at least one organic light-emitting diode according to claim 10.

15. The carbene complex according to claim 1, wherein M is Fe, Os, Co, Rh, Ir, Ni, Ru, Pd, Pt, Cu, Au, Ce, Tb, or Eu.

16. The carbene complex according to claim 3, wherein $R^3$ is selected from the group consisting of methyl, ethyl, n-propyl, isopropyl, n-butyl, isobutyl, sec-butyl, tert-butyl, tolyl, dimethylphenyl, trimethylphenyl, pyridyl, thienyl, pyrrolyl, furyl, thiazolyl, oxazolyl, pyrazolyl, imidazolyl, methoxy, phenoxy, $SCH_3$, SPh, $SiR^4R^5R^6$, F, Cl, Br, $CF_3$, and CN.

17. The carbene complex according to claim 1, wherein L is a monoanionic ligand.

18. The carbene complex according to claim 1, wherein X is N.

19. The carbene complex according to claim 4, wherein $R^2$ is selected from the group consisting of isopropyl, isobutyl, isopentyl, sec-butyl, tert-butyl, 2-tolyl, 2-methoxyphenyl, 2-cyanophenyl, 2-trifluoromethylphenyl, 2,6-difluorophenyl, 2,3-, 2,4-, 2,5- and 2,6-dimethylphenyl or 2,4,6-, 2,3,4- and 2,3,5-trimethylphenyl; pyridin-2-yl, pyridin-3-yl, pyridin-4-yl, thiophen-2-yl, thiophen-3-yl, pyrrol-2-yl, pyrrol-3-yl, furan-2-yl, furan-3-yl, thiazol-2-yl, oxazol-2-yl, pyrazol-3-yl and imidazol-2-yl.

* * * * *